(12) United States Patent
Bein et al.

(10) Patent No.: US 10,751,290 B2
(45) Date of Patent: Aug. 25, 2020

(54) MESOPOROUS CALCIUM PHOSPHATE-CITRATE NANOPARTICLES AND USES THEREOF

(71) Applicants: Thomas Bein, Gräfelfing (DE); Constantin Freiherr Von Schirnding, Gräfelfing (DE); Hanna Engelke, München (DE); Johann Feckl, München (DE); Ludwig-Maximilians-Universität München, München (DE)

(72) Inventors: Thomas Bein, Gräfelfing (DE); Constantin Freiherr Von Schirnding, Gräfelfing (DE); Hanna Engelke, München (DE); Johann Feckl, München (DE)

( * ) Notice: Subject to any disclaimer, the term of this patent is extended or adjusted under 35 U.S.C. 154(b) by 0 days.

(21) Appl. No.: 15/749,886

(22) PCT Filed: Jul. 29, 2016

(86) PCT No.: PCT/EP2016/068231
§ 371 (c)(1),
(2) Date: Feb. 2, 2018

(87) PCT Pub. No.: WO2017/025359
PCT Pub. Date: Feb. 16, 2017

(65) Prior Publication Data
US 2018/0228735 A1 Aug. 16, 2018

(30) Foreign Application Priority Data

Aug. 11, 2015 (EP) .................... 15180540

(51) Int. Cl.
| | | |
|---|---|---|
| *A61K 47/02* | (2006.01) |
| *A61K 47/12* | (2006.01) |
| *A61K 47/24* | (2006.01) |
| *A61K 47/42* | (2017.01) |
| *A61K 9/51* | (2006.01) |
| *A61K 9/127* | (2006.01) |
| *C01B 25/32* | (2006.01) |
| *A61K 47/18* | (2017.01) |
| *B82Y 5/00* | (2011.01) |
| *B82Y 30/00* | (2011.01) |
| *B82Y 40/00* | (2011.01) |
| *C02F 1/28* | (2006.01) |
| *C05B 17/00* | (2006.01) |

(52) U.S. Cl.
CPC .......... *A61K 9/5115* (2013.01); *A61K 9/1272* (2013.01); *A61K 47/02* (2013.01); *A61K 47/12* (2013.01); *A61K 47/186* (2013.01); *A61K 47/24* (2013.01); *A61K 47/42* (2013.01); *C01B 25/32* (2013.01); *B82Y 5/00* (2013.01); *B82Y 30/00* (2013.01); *B82Y 40/00* (2013.01); *C01P 2004/64* (2013.01); *C01P 2006/12* (2013.01); *C01P 2006/14* (2013.01); *C01P 2006/16* (2013.01); *C02F 1/288* (2013.01); *C05B 17/00* (2013.01)

(58) Field of Classification Search
None
See application file for complete search history.

(56) References Cited

U.S. PATENT DOCUMENTS

2012/0201872 A1 8/2012 Huang

FOREIGN PATENT DOCUMENTS

| CN | 101428779 A | 5/2009 |
| CN | 104355297 A | 2/2015 |

OTHER PUBLICATIONS

McGann et al.(Amorphouscalcium phosphate in casein micelles of bovine milk Calcified Tissue International (1983), vol. 335, No. 6, pp. 821-823, 24 refs.). (Year: 1983).*
Zhang et al., Novel Mesoporous Silica Materials with Hierarchically Ordered Nanochannel: Synthesis with the Assistance of Straight-Chain Alkanes and Application, Journal of Chemistry vol. 2016, Article ID 5146573, 16 pages (Year: 2016).*
Lavasanifar et al., The effect of alkyl core structure on micellar properties of poly(ethylene oxide)-block-poly(L-aspartamide) derivatives, Colloids and Surfaces B: Biointerfaces 22 (2001) 115-126 (Year: 2001).*
Lee et al., Calculations of Critical Micelle Concentration by Dissipative Particle Dynamics Simulations: The Role of Chain Rigidity, J. Phys. Chem. B 2013, 117, 10304-10310 (Year: 2013).*
Woodford, Enlargement of taurocholate micelles by added cholesterol and monoolein: self-diffusion measurements, Journaolf Lipidr Esearchv Olume 10, pp. 539-545, 1969 (Year: 1969).*
Jacobs, E. E. et al., "Sodium Citrate Stabilized Calcium Phosphate Nanoparticles for the Sustained Delivery of Displatin." Society for Biomaterials, 2013, Abstract #57; retrieved from the Internet URL: <http://abstracts.biomaterials.org/data/papers/2013/0243-000720.pdf>.

(Continued)

*Primary Examiner* — Alton N Pryor
(74) *Attorney, Agent, or Firm* — Saliwanchik, Lloyd & Eisenschenk

(57) ABSTRACT

The present invention relates to mesoporous calcium phosphate-citrate nanoparticles, optionally comprising a lipid membrane, and pharmaceutical compositions thereof. The present invention further relates to a method of synthesizing the mesoporous calcium phosphate-citrate nanoparticles. The present invention relates to their use as drug delivery system. The present invention further relates to medical uses as bone or teeth cement, bone material or taste or non-taste masked carrier or delivery system. The present invention relates to the use of the mesoporous calcium phosphate-citrate nanoparticles in the diagnosis and/or treatment of cancer. The present invention further relates to the use of the mesoporous calcium phosphate-citrate nanoparticles in fertilizer or absorber of metal ions from wastewater and/or water.

20 Claims, 25 Drawing Sheets

(56) References Cited

OTHER PUBLICATIONS

Li, J. et al., "Calcium phosphate nanoparticles with an asymmetric lipid bilayer coating for siRNA delivery to the tumor." Journal of Controlled Release, 2012, 158(1): 108-114.
Mitsionis, A. I. et al., "The effect of citric acid on the sintering of calcium phosphate bioceramics." Ceramics International, 2010, 36(2): 623-634.

* cited by examiner

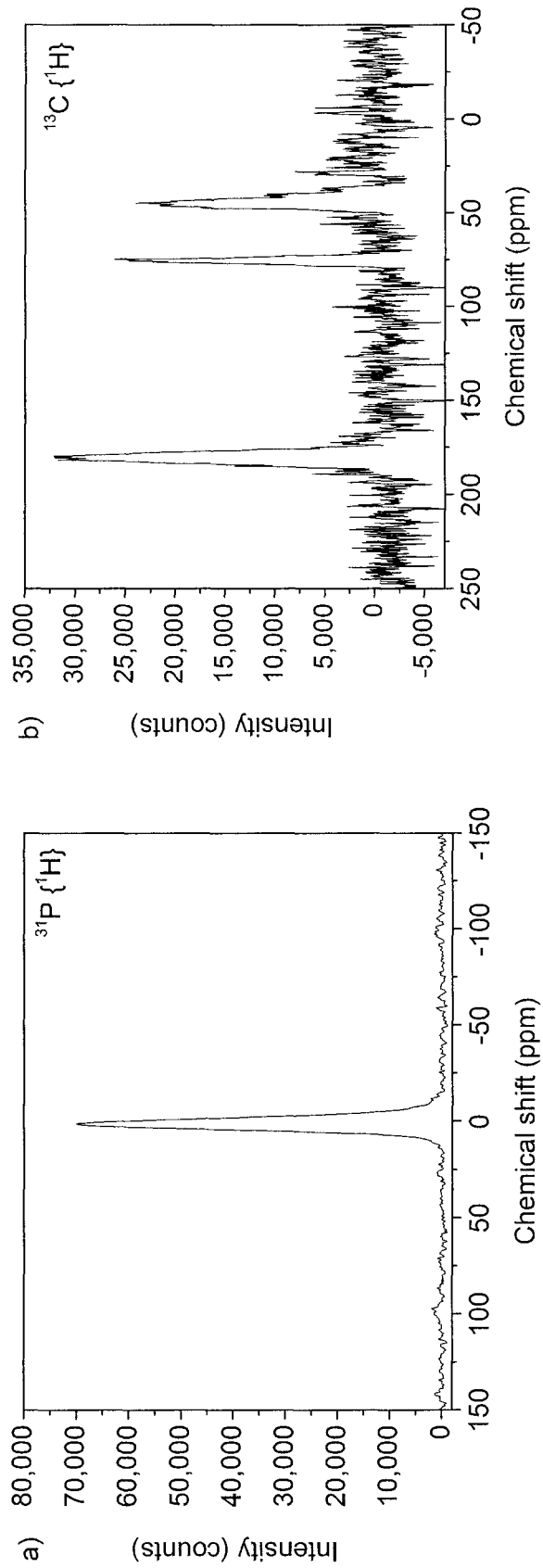
Figure 3 a and b

Figure 4 a and b

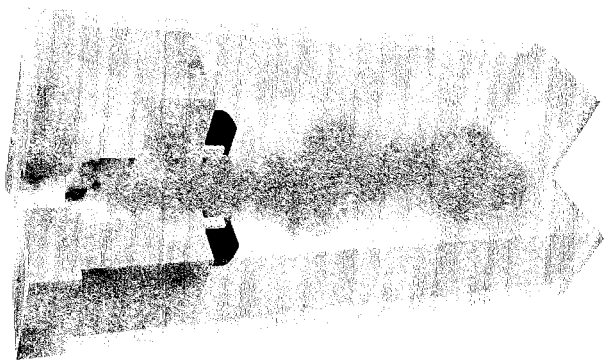
b
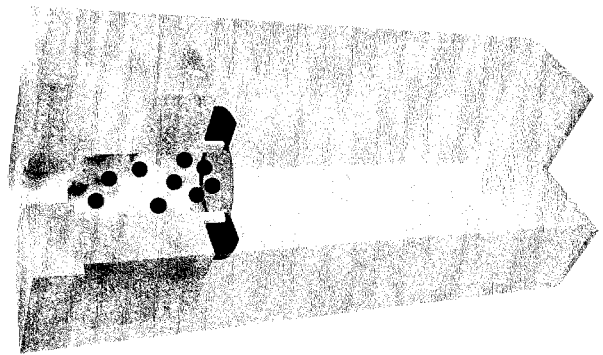
a
Figure 6

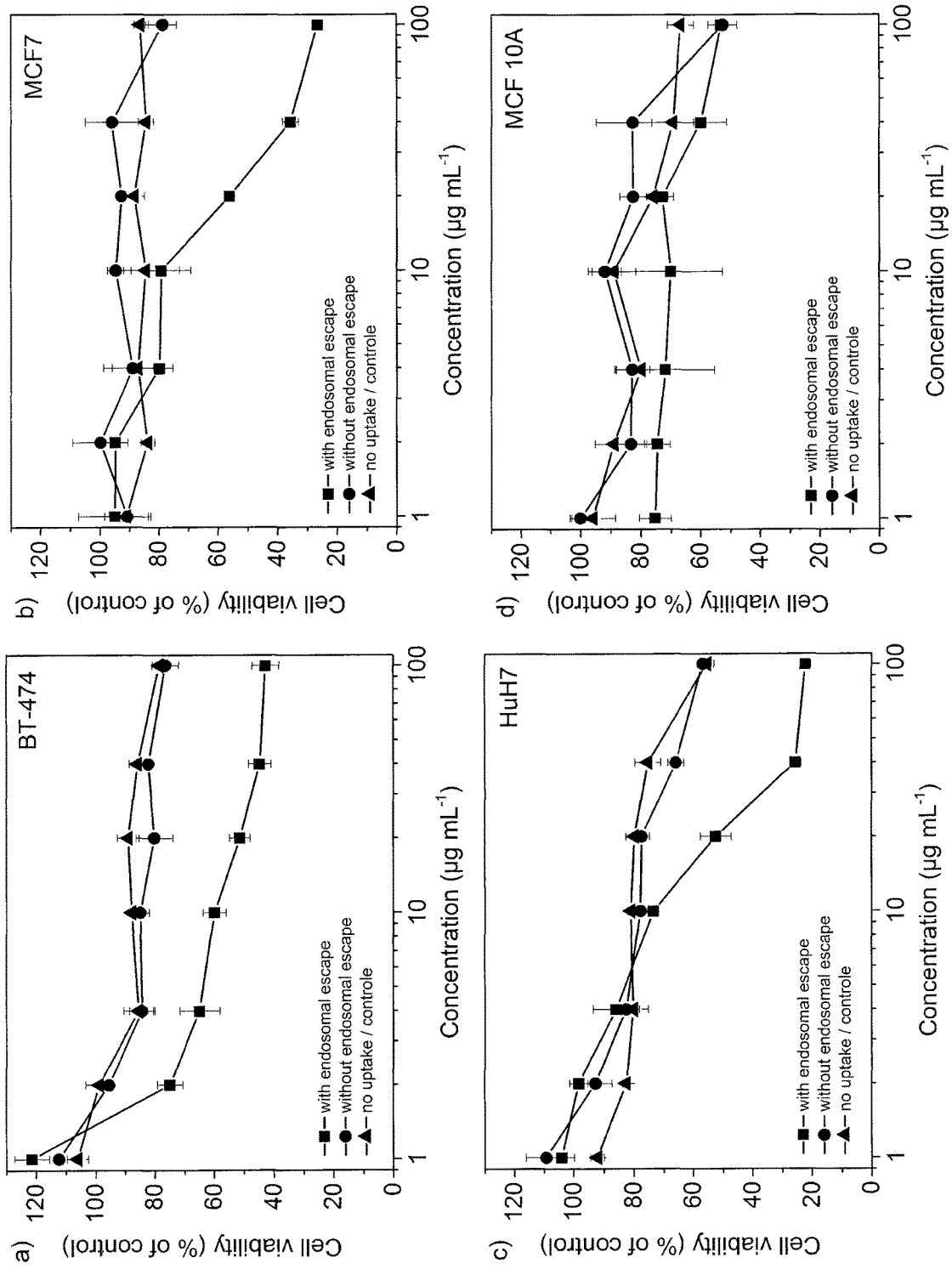
Figure 9 a-d

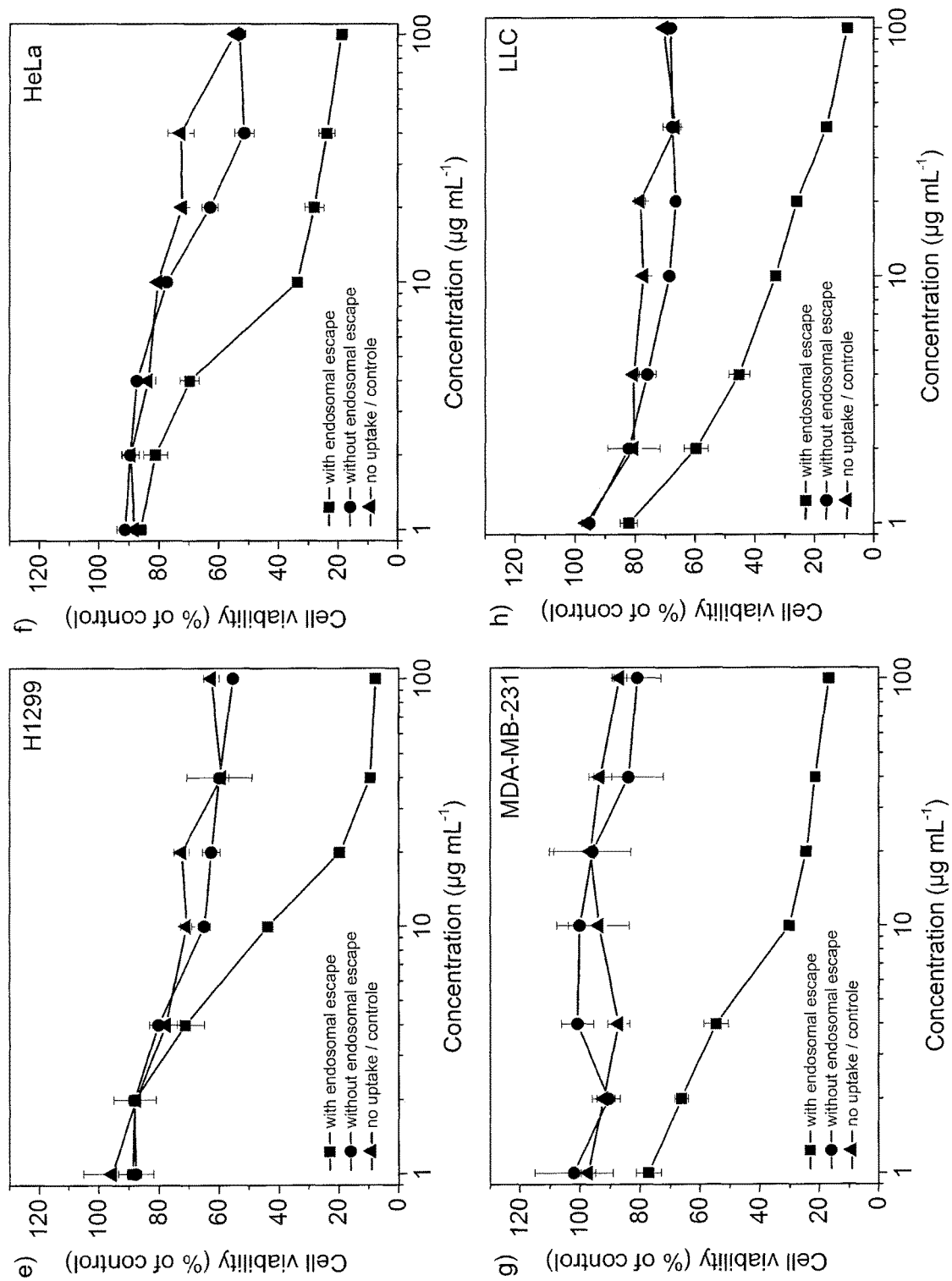

Figure 9 i und j
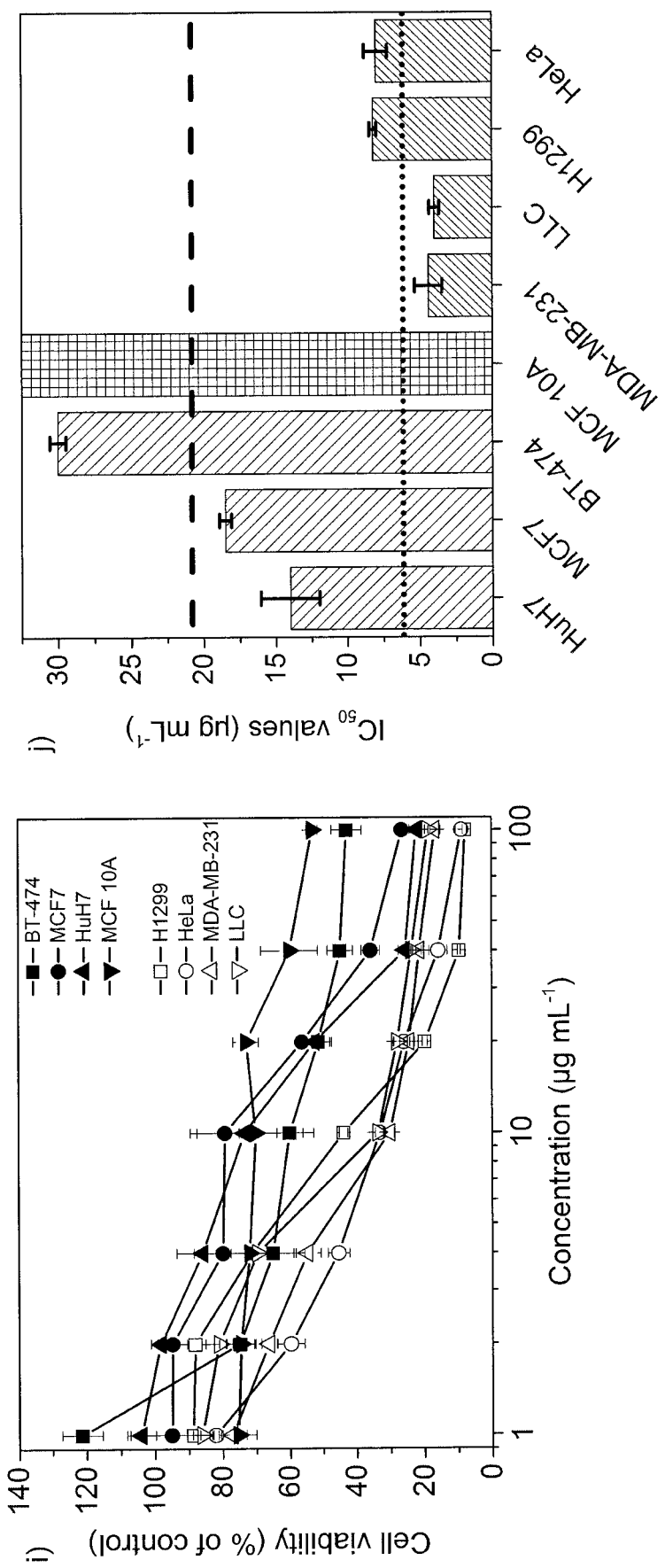

Figure 15
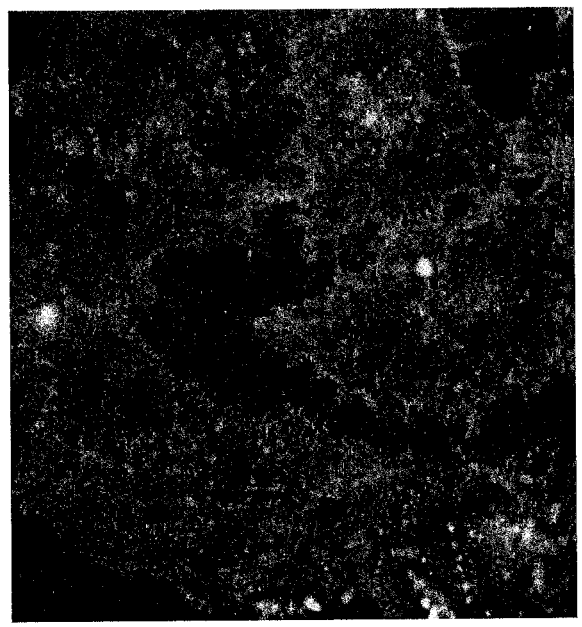
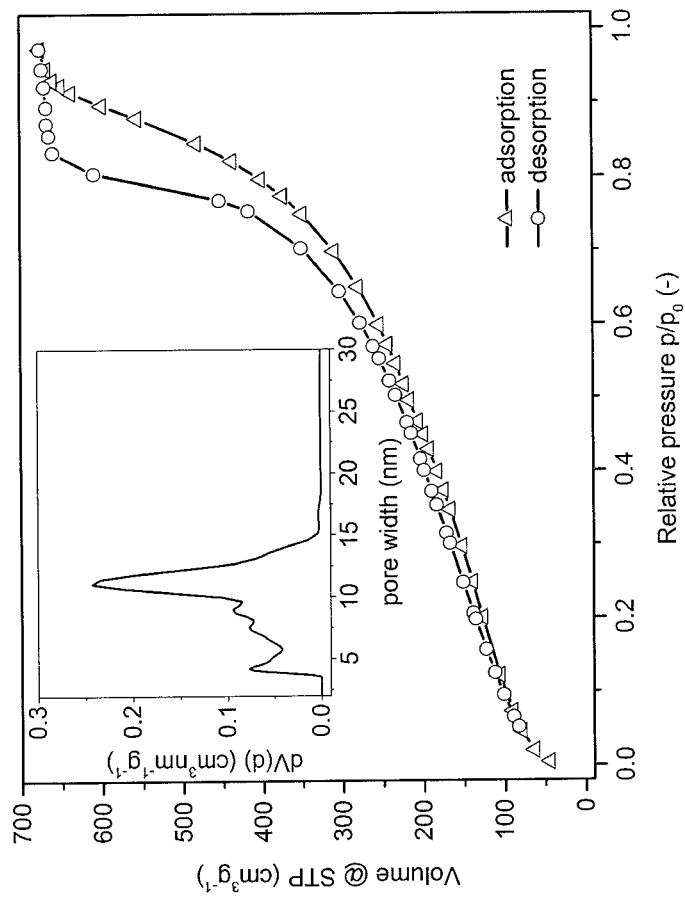

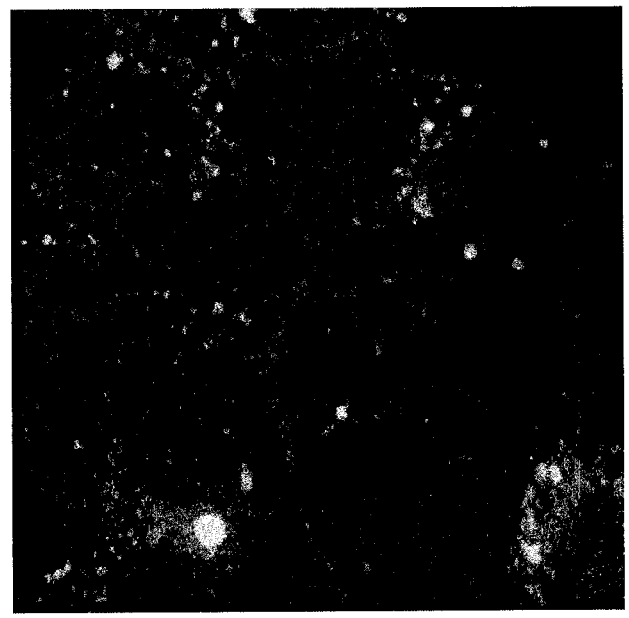
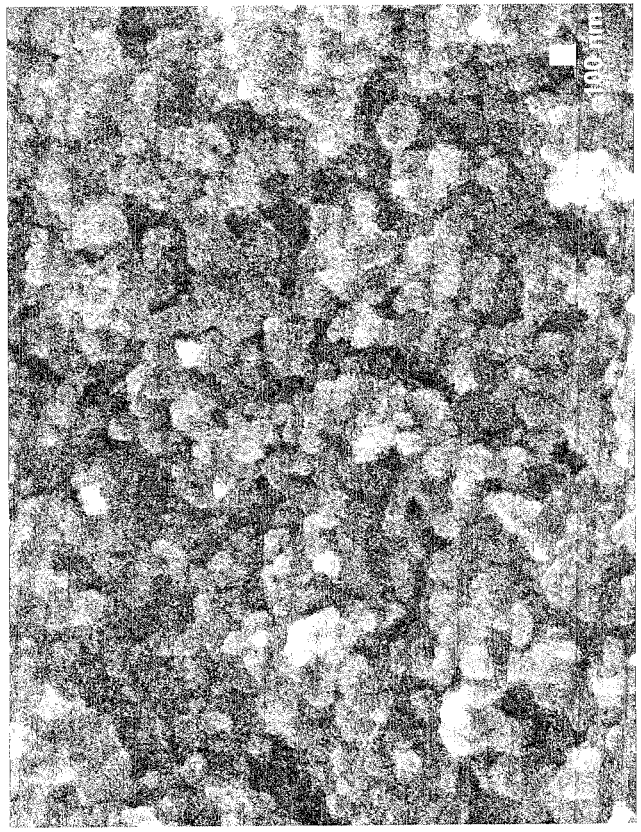
Figure 22

MESOPOROUS CALCIUM PHOSPHATE-CITRATE NANOPARTICLES AND USES THEREOF

CROSS REFERENCE TO A RELATED APPLICATIONS

This application is a National Stage Application of International Application Number PCT/EP2016/068231, filed Jul. 29, 2016; which claims priority to European Patent Application No. 15180540.5, filed Aug. 11, 2015.

The present invention relates to mesoporous calcium phosphate-citrate nanoparticles, optionally comprising a lipid membrane, and pharmaceutical compositions thereof. The present invention further relates to a method of synthesizing the mesoporous calcium phosphate-citrate nanoparticles. The present invention relates to their use as drug delivery system. The present invention further relates to medical uses as bone or teeth cement, bone material or taste or non-taste masked carrier or delivery system. The present invention relates to the use of the mesoporous calcium phosphate-citrate nanoparticles in the diagnosis and/or treatment of cancer. The present invention further relates to the use of the mesoporous calcium phosphate-citrate nanoparticles in fertilizer or absorber of metal ions from wastewater and/or water.

BACKGROUND OF THE INVENTION

Established anticancer chemotherapeutics (such as cisplatin, doxorubicin, fluorouracil) are injected into the bloodstream or administered as tablets by swallowing. To successfully treat cancer cells the patient must receive high doses of chemotherapeutics. Because the conventional chemotherapeutics are not able to distinguish well between cancerous or healthy tissue, the patient usually suffers from strong side effects.

Recent strategies in chemotherapy are based on the principle of transporting the chemotherapeutics directly to the cancerous cells and therefore specifically attack the cancer cells while the healthy cells survive. Cancerous cells exhibit modified proteins on the cell membrane that enables a targeted recognition of the cells. With so-called antibody-drug conjugates (Chari et al., 2014), one active chemotherapeutic molecule per antibody can be transported to cancer cells. To enhance the efficiency of the targeted transport, nanoparticles have attracted increasing attention. For example, mesoporous silica particles, polymer constructs, liposomes, dendrimers or DNA origami objects have been investigated in this context. Nanoparticles can be transported to cancer cells either passively (e.g. through the EPR-effect) or they can interact more specifically with certain cell types through targeting. Nanoparticles can be taken up by cancer cells through endocytosis. The internalized particles or their cargo must then escape from the endosome to release the encapsulated drug and to kill the cancer cell. Generally, in case of transport through nanoparticles, the delivery system remains in the cell and must be degraded or removed from the body as extrinsic material. Furthermore, the toxic substances delivered to the cancer cells remain in the body and could lead to damage before their removal or if they leak out of the drug delivery system. In addition to epithelial cancer cells, mesenchymal cancer cells present a serious issue in oncology. They enable the tumor to recover after conventional chemotherapy and may spread the tumor all over the body by creating metastases. Only very few substances are known for the successful treatment of this mesenchymal cancer cell type (e. g. salinomycin, etoposide, abamectin, nigericin) (Gupta et al., 2009).

The transport system, so called drug delivery vehicles, benefits from certain characteristics such as high porosity/capacity for efficient loading with drug molecules, good biocompatibility and biodegradability, and a suitable size and shape for efficient cell uptake. Several materials, such as mesoporous silica particles, liposomes, polymer constructs, or dendrimers have been published that are intended to combine the above requirements within one drug delivery system.

These systems need to be designed such that premature release of the toxic drugs is prevented. As mentioned above, targeting, endocytosis and endosomal escape need to be achieved to ensure effective delivery of the drugs to the target cells. Specifically, endosomal escape has been achieved with photochemical methods (Mackowiak et al., 2013; Schlossbauer et al., 2012), temperature dependent mechanisms (Schlossbauer et al., 2010) or pH-responsive systems (Varkouhi et al., 2011; Behr et al., 1997).

Generally, the backbone of the drug delivery system remains in the body and must be degraded and removed from the body as extrinsic material.

Therefore, a major goal in the development of drug delivery systems is to increase the biocompatibility of the backbone. As an example, the PEGylation of silica nanoparticles has been investigated to eliminate hemolysis (Lin and Haynes 2010) or to avoid the activation of the immune system (He et al., 2010).

The utilization of drug delivery systems opens up many possibilities in cancer treatment, for example: the protection and transport of sensible drug molecules, the easy exchangeability of drugs, the reduction of dosage, the increase of circulation time, the increase of drug concentration at the targeted site, and the opportunity to design a personalized medication. Generally speaking, it would constitute a major advance in drug delivery if highly toxic substances could be avoided altogether.

Recently, apatite $Ca_{10}(PO_4)_6(OH)_2$, the main inorganic component of natural bone and teeth, has been discussed as a new promising platform for advanced drug delivery applications due to its high biocompatibility and non-toxicity (Iafisco et al., 2009; Dorozhkin and Epple, 2002; Palmer et al., 2008). Furthermore, apatite is known to be biodegradable (Arcos and Vallet-Regi, 2013) and as a result could solve the problem of eliminating the transport material from the body. However, calcium phosphate-based materials suffer from some drawbacks regarding applications in drug delivery systems. The maximum known surface area for calcium phosphate-based compounds is published to be 315 $m^2\ g^{-1}$ which limits the loading capacity (Chen et al., 2014). Nevertheless, porous calcium phosphate based compounds were loaded with docetaxel (Chen et al., 2014; Ding et al., 2015), silybin (Chen et al., 2015) ibuprofen (Zhao et al., 2012) and doxorubicin (Rodriguez-Ruiz et al., 2013).

Next to loading drugs into the network of porous calcium phosphate particles, there have been investigations on co-precipitation methods of $Ca^{2+}$- and $PO_4^{3-}$-ions with Gemcitabine, siRNA, or proteins (Li et al., 2012; Zhang et al., 2013). The co-precipitated particles were delivered to cells, endosomal release due to the proton sponge effect was observed, and the function of the drug was proven. With an approach like this, the used molecules must be stable and soluble under the reaction conditions of co-precipitation. Because most drug molecules are not very soluble in water and therefore not suitable for water based co-precipitation methods, the authors (Li et al., 2012; Zhang et al., 2013) introduced a water-in-oil based synthesis approach.

However, if an exchange of the drug is desired, the reaction conditions must be adjusted again because all molecules take part in the reaction and may influence the required synthesis conditions and the properties of the particles. Moreover, the shape of the calcium phosphate based nanoparticles plays an important role regarding cell viability. The toxic effect of calcium phosphate nanoparticles was investigated for non-porous plate-, rod-, or needle-shaped, as well as spherical morphologies on two human cell lines (Zhao et al., 2013-a). Cell death was more pronounced with plate- and needle-shaped than with spherical- or rod-shaped structures at concentrations above 100 μg mL$^{-1}$. In another publication cell death was observed with non-porous, rod-like particles on gastric cancer cells, cervical adenocarcinoma epithelial cells and hepatoma cells, whereas no cell death was observed for normal human hepatocyte cells at concentrations higher than 125 μg mL$^{-1}$ (Tang et al., 2014). Below these high concentrations there has been no sign for cell death in either of these publications. The influence of the particle synthesis with respect to their toxicity was investigated in another publication on a macrophage cell line, and toxicity was highest for an autoclave synthesis approach with gel-like rod-shaped nanoapatite at concentrations higher than 125 μg mL$^{-1}$ (Motskin et al., 2009). In contrast, nanocrystalline apatite is said to be biocompatible to a final concentration of 100 μg mL$^{-1}$ (Delgado-Lopez et al., 2012). Therefore, the definition of biocompatibility with respect to calcium phosphate based nanoparticles still appears to be controversial.

In some instances, citric acid has been used as a synthetic aid for the preparation of crystalline calcium phosphate particles and nanoparticles. In the corresponding prior art, none of these particles and nanoparticles combine amorphous structure and internal mesoporosity. In contrast, they form agglomerates or aggregates having textural pores between the constituent domains of the agglomerates or aggregates. This textural porosity differs significantly from mesoporosity resulting from holes inside individual particles.

For example, Mitsionis et al. (2010) disclose the effect of citric acid on the synthesis of high temperature-sintered calcium phosphate ceramics, consisting of crystalline calcium phosphate with textural porosity.

For example, Chinese patent application no. CN 104 355 297 A describes crystalline calcium phosphate, namely hydroxyapatite, particles or nanoparticles that are made of dried bulk material consisting of intergrown nanoscale crystallites. CN 104 355 297 A describes a method for synthesizing a microemulsion of hydroxyapatite, wherein said method utilizes cetyltrimethylammonium bromide (CTAB) or citric acid as tension-active agent, which is not used as structure directing template. The resulting bulk material consists of inorganic materials without the included organic materials of a hybrid compound. Textural porosity generated by agglomeration of crystalline particles with aperture diameters of 19.56-40.13 nm are described. The surface structure of the crystalline bulk material thus contains "holes" at which compounds or drugs can be absorbed. Therefore, the generated pores are not within the single colloidal stable nanoparticles but result from the agglomeration of intergrown nanoscale domains at the external surface.

For example, Chinese patent application no. CN 101 428 779 A describes hollow nanostructured crystalline hydroxyapatite and a preparation method thereof. Citric acid and EDTA are used as sequestrants to avoid precipitation of calcium phosphate at pH 5.2.

Furthermore, Jacobs et al. (2013) disclose non-porous sodium citrate stabilized calcium phosphate nanoparticles for the sustained delivery of the chemotherapeutic agent cisplatin. In these nanoparticles citrate is loosely attached and/or coordinated to the outer surface of the nanoparticles and protects and/or stabilizes the calcium phosphate, e.g. from agglomeration or degradation. The chemotherapeutic agent cisplatin is only absorbed on the outer surface of the nanoparticles without a functional triggered release mechanism.

There is a need in the art for improved means and methods for targeted delivery of compounds, in particular for biocompatible drug delivery systems, such as for targeted and controlled release particularly in cancer treatment.

SUMMARY OF THE INVENTION

According to the present invention this objective is solved by a mesoporous (hybrid) calcium phosphate-citrate nanoparticle comprising
(a) calcium phosphate, and
(b) citrate.

The mesoporous calcium phosphate-citrate nanoparticles of the present invention are preferably amorphous.

The term "hybrid nanoparticle" and "nanoparticle" is used interchangeably within this specification and refers to the mesoporous calcium phosphate-citrate nanoparticles of the present invention.

According to the present invention this objective is solved by a method for synthesizing/generating mesoporous hybrid calcium phosphate-citrate nanoparticles, preferably nanoparticles of the present invention, comprising the steps of
(1) mixing calcium ions ($Ca^{2+}$) and phosphate ions ($PO_4^{3-}$) with a complexing agent, preferably citric acid,
(2) optionally, adding templates,
such as cetyltrimethylammonium halide(s), Pluronic F127, polyethylene glycol, block copolymers, octadecyltrimethylammonium halide(s), dodecyltrimethylammonium halide(s) or micelle-enlarging molecules or further surfactants,
(3) precipitating the nanoparticles by changing the pH with a base, such as ethanolamine, triethanolamine, a biogenic base or an inorganic base,
(4) optionally, extracting the template(s), and
(5) obtaining the nanoparticles.

According to the present invention this objective is solved by a nanoparticle obtained by a method of the present invention.

According to the present invention this objective is solved by a pharmaceutical composition, comprising
(i) at least one nanoparticle of the present invention and/or at least one nanoparticle obtained by the method of the present invention,
(ii) optionally, pharmaceutically acceptable carrier(s) and/or excipients.

According to the present invention this objective is solved by using a nanoparticle of the present invention or a nanoparticle obtained by a method of the present invention as drug delivery system, preferably with controlled release.

According to the present invention this objective is solved by providing a nanoparticle of the present invention or a nanoparticle obtained by a method of the present invention or a pharmaceutical composition of the present invention for use as a medicament.

According to the present invention this objective is solved by providing a nanoparticle of the present invention or a nanoparticle obtained by a method of the present invention or a pharmaceutical composition of the present invention for use as drug delivery system, preferably with controlled release, for bone cement or bone implant or teeth cement, for teeth or medical implants, preferably as drug reservoir, for coatings of medical implants, preferably as drug reservoir, bone material, such as in orthopedic applications, taste or non-taste masked carrier or delivery system, such as for tablet applications, chemotherapeutics.

According to the present invention this objective is solved by providing a nanoparticle of the present invention or a nanoparticle obtained by a method of the present invention or a pharmaceutical composition of the present invention for use in the diagnosis and/or treatment of cancer.

According to the present invention this objective is solved by using a nanoparticle of the present invention or a nanoparticle obtained by a method of the present invention as fertilizer, preferably as phosphate source in fertilizer.

According to the present invention this objective is solved by using a nanoparticle of the present invention or a nanoparticle obtained by a method of the present invention as absorber for metal ions from wastewater and/or water.

According to the present invention this objective is solved by a method for the diagnosis and/or treatment of cancer, comprising the step of administering to a subject in need thereof a therapeutically effective amount of a nanoparticle of the present invention, a nanoparticle obtained by the method of the present invention, or a pharmaceutical composition of the present invention.

According to the present invention this objective is solved by a drug delivery system, preferably with controlled release, comprising a nanoparticle of the present invention, a nanoparticle obtained by the method of the present invention, or a pharmaceutical composition of the present invention.

According to the present invention this objective is solved by a bone cement or bone implant or teeth cement or a teeth implant or a drug reservoir/delivery system for bone cement or bone implant or teeth cement or a teeth implant, comprising a nanoparticle of the present invention, a nanoparticle obtained by the method of the present invention, or a pharmaceutical composition of the present invention.

According to the present invention this objective is solved by a coating of medical implants (e.g. stents) or a drug reservoir/delivery system for coating of medical implants, comprising a nanoparticle of the present invention, a nanoparticle obtained by the method of the present invention, or a pharmaceutical composition of the present invention.

According to the present invention this objective is solved by a bone material, comprising a nanoparticle of the present invention, a nanoparticle obtained by the method of the present invention, or a pharmaceutical composition of the present invention.

According to the present invention this objective is solved by a carrier or delivery system with or without taste masking, comprising a nanoparticle of the present invention, a nanoparticle obtained by the method of the present invention, or a pharmaceutical composition of the present invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "1 to 50 nm" should be interpreted to include not only the explicitly recited values of 1 to 50, but also include individual values and sub-ranges within the indicated range. Thus, included in this numerical range are individual values such as 1, 2, 3, 4, 5, . . . 47, 48, 19, 50 and sub-ranges such as from 1 to 20, from 10 to 20, from 10 to 30, from 10 to 25, from 20 to 25, from 25 to 45, from 20 to 30 and from 15 to 30, etc. This same principle applies to ranges reciting only one numerical value, such as "at least 1 nm" or "up to 300 nm". Furthermore, such an interpretation should apply regardless of the breadth of the range or the characteristics being described.

Mesoporous calcium phosphate-citrate nanoparticles

The present invention provides a highly mesoporous hybrid calcium phosphate-citrate nanoparticle/mesoporous calcium phosphate-citrate nanoparticle which can be flexibly loaded, such as with different water- or nonwater-soluble drugs. The adsorbed drugs are preferably kept inside the colloidal particles by a lipid membrane until they are taken up by cells. Because of the lipid membrane it is possible to additionally enhance the passive uptake with additional targeting ligands. The particles preferably kill cancerous epithelial cell lines with similar efficiency as the chemotherapeutic doxorubicin. In addition, cancerous mesenchymal cell lines are efficiently killed by the particles described in our invention, which thus extends the small group of substances that can selectively kill this resistant cell type. In contrast, the internalized particles show no harmful effect towards non-tumorigenic cell lines. If the particles are not taken up by cells at all, which we can control with the lipid membrane, or if they do not escape from the endosome, which we can control with the amount of additives, such as cetyltrimethylammonium chloride (CTAC), our results show no toxic effect to any cell line investigated so far. Therefore, we provide an efficient, inexpensive and biocompatible approach towards chemotherapy.

In addition to this application, our porous calcium phosphate-citrate particles can function as a drug reservoir for bone- and teeth-cements or as coating for medical implants. Also, our new material can find usage as taste-free drug delivery system for oral tablet administration. Furthermore, it is suitable as a novel concept for easily available fertilizer applications. Additionally, the porous particles can find application as absorber of metal ions from wastewater.

As discussed above, the present invention provides mesoporous hybrid calcium phosphate-citrate nanoparticles.

Said mesoporous hybrid calcium phosphate-citrate nanoparticles/mesoporous calcium phosphate-citrate nanoparticles comprise
(a) calcium phosphate, and
(b) citrate.

The term "hybrid" nanoparticle as used herein refers to the combination of inorganic elements with organic elements.

The term "hybrid" is defined by IUPAC (2007):
4.1.14 hybrid material
Material composed of an intimate mixture of inorganic components, organic components, or both types of component.
Note: The components usually interpenetrate on scales of less than 1 μm.

With the term "hybrid", the combination of the inorganic part or elements of the nanoparticles, namely calcium phosphate, with the organic part or elements of the nanoparticle, namely organic acid(s), in particular citric acid, is emphasized.

However, the term "hybrid nanoparticle" and "nanoparticle" is used interchangeably within this specification and refers to the mesoporous calcium phosphate-citrate nanoparticles of the present invention.

The term "mesoporous" as used herein refers, according to IUPAC recommendations (Rouquerol, 1994), to pores with free diameters in the range of 2 to 50 nm.

The pores with "free diameters" refer to the pore diameter measured in the dried state with a measurement technique such as the determination of nitrogen sorption isotherms, and analysis methods such as Density Functional Theory (DFT) or the method of Barrett, Joyner, and Halenda (BJH method), which is employed to extract pore size distributions from experimental isotherms on the basis of the Kelvin model of pore filling.

Furthermore, the mesoporous nanoparticles of the present invention have their internal mesopores within individual nanoparticles. They are to be distinguished from agglomerated nanoparticles, which form holes between the nanoparticles/domains. Such pores resulting from the agglomeration of several particles are referred to as textural porosity.

Mesoporosity can be shown and visualized with sorption measurements, for example by measuring the sorption isotherm of nitrogen (Sing, 1985). A typical type IV sorption isotherm (indicating a narrow pore size distribution) is characteristic of mesoporous systems, as in the nanoparticles of the present invention with their internal mesoporosity. See FIGS. 4a and b, as an example.

In contrast, type II and type III sorption isotherms are characteristic for nonporous solids, including aggregates having interspaces between the particles in the aggregates, i.e. so called textural mesoporosity. For example, Mitsionis et al. (2010), FIG. 10, describe calcium phosphate materials showing a type III sorption isotherm.

The mesoporosity can further be shown and visualized in Transmission Electron Microscopy (TEM) images. TEM images taken in bright field imaging mode show a variation in contrast between bright and dark areas within one displayed particle, the bright parts representing the regions where electrons interact less with the material. These regions correspond to pores in the material.

See FIG. 1c, as an example.

Preferably, the nanoparticles of the present invention have
a maximum surface area from about 100 to about 1500 $m^2/g$, preferably from about 500 to about 1200 $m^2/g$, more preferably about 900 $m^2/g$,
a pore size from about 1 to about 50 nm, preferably from about 1 to about 20 nm, more preferably about 4.5 nm, and/or
a cumulative pore volume from about 0.1 to 2.0 $cm^3/g$, preferably from about 0.3 to about 1.5 $cm^3/g$. more preferably about 1.0 $cm^3/g$.

Preferably, the nanoparticles of the present invention have a maximum size from about 5 to about 1000 nm, preferably about 5 to about 999 nm, preferably from about 30 to about 500 nm,
and/or are spherical particles, preferably with about 50 nm in average measured with TEM.

The "maximum size" refers to the diameter of the nanoparticles of the present invention.

For example, the nanoparticles of the present invention have an average size or diameter of about 220 nm in ethanolic solution measured with dynamic light scattering (DLS).

The preferred size (diameter) of the nanoparticles of the present invention will depend on the intended use. For example, nanoparticles of the present invention to be used as drug delivery systems and/or for targeting cancer cells, will have a preferred (maximum) size (diameter) of up to about 300-400 nm (in order to allow endocytosis). For example, nanoparticles of the present invention to be used differently, such as bone cement, oral drug or fertilizer or absorber, can be bigger in size (diameter), for example above 1000 nm.

Preferably, the nanoparticles of the present invention comprise from about 0.01 to about 60 w % of citric acid, preferably 1 to 25 w % of citric acid, more preferably about 20 w % of citric acid.

Preferably, the nanoparticles of the present invention have IR C—O vibrational bands at around 1590 $cm^{-1}$ and 1400 $cm^{-1}$.

This feature can be used to distinguish the mesoporous nanoparticles of the present invention from nanoparticles of the prior art. It shows that citrate is incorporated in the structure of the nanoparticles.

These bands show increasing intensity with increasing amount of citrate incorporated into the structure. FIG. 2 for example shows vibrational bands at 1590 $cm^{-1}$ and 1400 $cm^{-1}$ that are much stronger for our invention as compared to hydroxyapatite, such as at least about 10% in intensity with respect to the phosphate vibration measured in absorbance mode.

The nanoparticles of the present invention can be furthermore characterized as being amorphous.

The nanoparticles of the present invention can be furthermore characterized as being colloidal in solution.

The term "amorphous" as used herein refers to a material having no long-range order in any direction of a three-dimensional system and therefore it refers to a non crystalline material.

The amount or degree of crystallinity can be measured and visualized via X-ray diffraction in XRD patterns: crystalline materials show defined peaks (see, e.g., FIGS. 1 and 2 of Mitsionis et al., 2010; or FIG. 1 1of CN 104 355 297 A, or FIGS. 1, 3, 5, 8, 11, 13, and 16 of CN 101 428 779 A), whereas amorphous materials do not show such defined peaks. See, e.g., FIG. 12, WAXS insert, as an example.

The term "colloidal" as used herein refers to nanoparticles that are dispersed in a liquid medium e.g. methanol, ethanol, water, hexane, toluene, dichlormethane, dimethylsulfoxide, acetonitrile, serum, blood, etc. and have a dimension of roughly 1 nm to 1 µm (IUPAC definition), and do not sediment as large aggregates. The nanoparticles of the present invention are colloidally stable over a significant time period, such as over weeks and/or months.

Colloidal stability can be shown and visualized via dynamic light scattering (DLS). The size of the particles is determined from their Brownian motion. This strongly depends on the solvent in which the particles are dispersed and the agglomeration behavior of the particles in that solvent. Due to electrostatic and other interactions that depend on the properties of the solvent and of the particles, particles can agglomerate to different degrees in different solvents or buffers and thus show different apparent sizes in different solvents.

See FIG. 1d, as an example.

In a preferred embodiment, the nanoparticles of the present invention further comprise
(c1) a lipid bilayer or lipid membrane. and/or
(c2) coating with polymers, capping with proteins, or exosomes/liposomes.

Preferably, said lipid bilayer or lipid membrane (c1) comprises
lipids such as 1,2-dioleoyl-3-trimethylammonium-propane (DOTAP), 1,2-dioleoyl-sn-glycero-3-phosphocholine (DOPC), phospholipids, sphingolipids, and/or
lipid-conjugated molecules, such as cholesterol, collagen, fatty acids, protamine, DNA, PEGylated lipid(s), dye conjugated lipid(s),
and/or further membrane-forming substances.

Preferably, said coating with polymers, capping with proteins, or exosomes/liposomes (c2) comprise PEG and/or PVP, layered double hydroxides, cyclodextrin, rotaxane, chitosan, polysaccharide(s), carboanhydrase and/or biotin-avidin and/or BSA.

In one embodiment, the nanoparticles of the present invention further comprise an additive.

Preferred additives are:
cetyltrimethylammonium halide(s), e.g. cetyltrimethylammonium chloride (CTAC) or cetyltrimethylammonium bromide (CTAB),
octadecyltrimethylammonium halide(s), e.g. octadecyltrimethylammonium chloride (OTAC) or octadecyltrimethylammonium bromide (OTAB),
dodecyltrimethylammonium halide(s),
reactive oxygen generating molecules or species,
or further surfactants or membrane destabilizing agents.

In one embodiment, Lysotracker® (Life Technologies of Thermo Fisher Scientific) are used as additives.

A "membrane destabilizing agent", when used as an additive in the present invention, refers to a compound/molecule that is capable of destabilizing/destroying a lipid membrane. It could also (but not only) be an adsorbed photosensitizer, which produces reactive oxygen species (ROS) upon illumination. Therefore, any molecule that is capable of destabilizing a lipid membrane can be used. The function of the "membrane destabilizing agent" as an additive is to destabilize and/or remove the lipid layer formed and the endosomal membrane when the particles are acidified in the endosome.

An "additive"—as used herein—is added and/or adsorbed to the porous structure of the nanoparticles and shows as main function but is not limited to the destabilization and/or destruction of the lipid layer around the nanoparticles, and/or the endosomal membrane.

In a preferred embodiment, the nanoparticles of the present invention further comprise further compound(s).

"Further compound"—as used herein—refers to compounds that are adsorbed to the particles' surface and/or into the particles' pore system and can later be released at their target region, such as cytosol, blood, skin, etc. These compounds cause effects other than just the destabilization and/or destruction of the lipid layer. For example, they induce cell death, reprogram cells, heal tissues and/or cells, etc.

Said further compound(s) are preferably selected from, but not limited to:
drug(s) or prodrug(s),
    such as
        chemotherapeutic agent(s),
        antibiotic(s),
        analgesic(s),
        anti-inflammatoric(s),
        peptide(s),
        protein(s),
        antibody(s),
        vaccine(s),
        DNA,
        RNA,
        cell membrane destabilizing agents,
        or combinations thereof,
label(s),
    such as fluorescent dye(s), radioisotope(s), quantum dot(s), superparamagnetic metal oxide nanoparticle(s), gold nanoparticle(s), metal cluster(s), complexing agent(s) or combinations thereof,
targeting ligand(s),
    such as epidermal growth factor (EGF), folic acid, arachidonic acid, antibody(s) (such as Herceptin and/or CD3, peptide(s) (such as RGD and/or NGR), protein(s) (such as transferrin), sugar(s) (such as galactosamine and/or galactose and/or mannose), aptamer(s) (such as AS1411, see Sun et al., 2014; Zhang et al., 2014) or combinations thereof,
pore-gating molecule(s),
    such as
        protein(s) including carboanhydrase and/or biotin-avidin and/or BSA,
        gold-nanoparticle(s),
        superparamagnetic iron oxide nanoparticle(s),
        oligonucleotide(s) such as DNA and/or RNA,
        lipid membranes,
        polymer(s) such as PEG and/or PVP, layered double hydroxides, cyclodextrin, rotaxane, chitosan, polysaccharide(s),
        or combinations thereof,
biocompatible polymer(s),
    such as polyethyleneglycol(s) (PEG), polyethyleneimine(s) (PEI), polyvinylchloride(s) (PVC), polyvinyl pyrrolidone (PVP),
anchoring group(s) at the nanoparticle,
    such as for covalently attaching further compound(s), including amines, thiols, carboxylic acids, hydroxides, azides,
anchoring group(s) at the lipid bilayer or membrane,
    such as for covalently attaching further compound(s), including amines, thiols, carboxylic acids, hydroxides, azides,
endosomal escape-triggers at the nanoparticle and/or at the lipid bilayer or membrane, such as pH-sensitive stimuli/triggers including polyethylenimine(s) (PEI), polyvinyl pyrrolidone(s) (PVP) and/or Lysotracker(s)®etc., such as light-sensitive stimuli/triggers including photosensitizer(s), switchable lipid(s) and/or polymer(s), such as temperature-dependent stimuli/triggers including DNA, lipid(s) and/or polymer(s), such as membrane destabilizing protein(s) including INF-7, such as membrane destabilizing molecules including CTAC, CTAB, OTAC, OTAB, fatty acids, Lysotracker®, dodecyltrimethylammonium halide(s);

(membrane) fusion triggering peptides;

such as SNARE proteins, or combinations thereof.

In one embodiment, the further compound(s) is/are comprised in the pores of the nanoparticle and/or (covalently) attached or adsorbed to the nanoparticle or to the (lipid) membrane.

Method of Synthesizing/Generating Calcium Phosphate-Citrate Nanoparticles

The present invention provides a method for synthesizing/generating calcium phosphate-citrate nanoparticles.

Preferably, the method is for synthesizing/generating the mesoporous hybrid calcium phosphate-citrate nanoparticles of the present invention.

Said method comprises the steps of (1) mixing calcium ions ($Ca^{2+}$) and phosphate ions ($PO_4^{3-}$) with a complexing agent, preferably citric acid, (2) optionally, adding templates, such as cetyltrimethylammonium halide(s), Pluronic F127, polyethylene glycol, block copolymers, octadecyltrimethylammonium halide(s), dodecyltrimethylammonium halide(s) or micelle-enlarging molecules or further surfactants, (3) precipitating the nanoparticles by changing the pH with a base, such as ethanolamine, triethanolamine, a biogenic base or an inorganic base, (4) optionally, extracting the template(s), and (5) obtaining the nanoparticles.

In one embodiment, wherein the method is for synthesizing/generating mesoporous calcium phosphate-citrate nanoparticles, the method comprises the steps of:

(1) mixing calcium ions ($Ca^{2+}$) and phosphate ions ($PO_4^{3-}$) with a complexing agent, preferably citric acid, (2) adding templates, such as cetyltrimethylammonium halide(s), Pluronic F127, polyethylene glycol, block copolymers, octadecyltrimethylammonium halide(s), dodecyltrimethylammonium halide(s) or micelle-enlarging molecules or further surfactants, (3) precipitating the nanoparticles by changing the pH with a base, such as ethanolamine, triethanolamine, a biogenic base or an inorganic base, (4) extracting the template(s), and (5) obtaining the mesoporous nanoparticles.

In one embodiment, wherein the method is for synthesizing/generating therapeutically active nanoparticles, the method comprises the steps of:

(1) mixing calcium ions ($Ca^{2+}$) and phosphate ions ($PO_4^{3-}$) with a complexing agent, preferably citric acid, (3) precipitating the nanoparticles by changing the pH with a base, such as ethanolamine, triethanolamine, a biogenic base or an inorganic base, and (5) obtaining the nanoparticles.

In one embodiment, calcium phosphate•citrate is used in step (1).

In one embodiment, in step (1)

the molar ratio of $Ca^{2+}$:citric acid is between 1:1 to 1:0.2, the molar ratio of $Ca^{2+}$:$PO_4^{3-}$ is between 1:0.76 to 1:0.45, such as about 1:0.66, and/or the molar ratio of $Ca^{2+}$:$PO_4^{3-}$:citric acid is about 5:3:5.

In one embodiment, $Ca(NO_3)_2$•4 $H_2O$ and/or other $Ca^{2+}$ salts are used as calcium source in step (1).

In one embodiment, $(NH_4)H_2PO_4$, and/or other $PO_4^{3-}$ salts/acids, adenosine-triphosphate, adenosine-diphosphate, and/or adenosine-monophosphate are used as phosphate source in step (1).

In one embodiment, the $OH^-$ ion of the "$Ca_5(PO_4)_3OH$"•citrate as used in step (1) is substituted or exchanged with halides or pseudo-halides.

In one embodiment, the $Ca^{2+}$ ion is substituted with different divalent cations, such as $Mg^{2+}$, $Ba^{2+}$, $Ti^{2+}$, $Fe^{2+}$, $Zn^{2+}$, $Pt^{2+}$, $Cu^{2+}$, lanthanides (e.g. $Eu^{2+}$), and/or the $PO_4^{3-}$ ion is substituted with carbonate, sulfate, borate, phosphonate, sulfonate, sulfonamide.

In a preferred embodiment, the $Ca^{2+}$ ions are substituted or replaced with $Mg^{2+}$ or the $Ca^{2+}$ ions are mixed with $Mg^{2+}$.

The resulting nanoparticles can thus be colloidal amorphous mesoporous magnesium phosphate-citrate nanoparticles or colloidal amorphous mesoporous calcium-magnesium phosphate-citrate nanoparticles, respectively. For completeness, the $Mg^{2+}$ of colloidal amorphous mesoporous magnesium phosphate-citrate nanoparticles could also be substituted or replaced with $Ca^{2+}$ or the $Mg^{2+}$ ion is mixed with $Ca^{2+}$. The resulting nanoparticles can thus be colloidal amorphous mesoporous magnesium-calcium phosphate-citrate nanoparticles Preferably, the template(s) added in step (2) is/are selected from cetyltrimethylammonium halide(s), such as cetyltrimethylammonium chloride (CTAC) or cetyltrimethylammonium bromide (CTAB), Pluronic F127, polyethylene glycol, block copolymers, octadecyltrimethylammonium halide(s), such as octadecyltrimethylammonium chloride (OTAC) or octadecyltrimethylammonium bromide (OTAB), dodecyltrimethylammonium halide(s), or micelle-enlarging molecules.

In one embodiment, the template for the pore structure (added in step (2)) varies in chain length, longer chains, like octadecyltrimethylammonium halide(s), such as octadecyltrimethylammonium chloride (OTAC) or octadecyltrimethylammonium bromide (OTAB);

shorter chains, like dodecyltrimethylammonium halide(s)—

In one embodiment, further biogenic surfactants and different polymers and/or micelle-enlarging molecules are used as further templates in step (2).

Regarding the precipitation step (3): Calcium phosphates precipitate only in basic medium when no pressure (e.g. hydrothermal synthesis) is applied. Thus, the use of a base for changing the pH is preferred.

In one embodiment, the base can be
triethanolamine,
a biogenic base, such as but not limited to lysine, histamine, arginine, histidine, (poly)ethyleneimine, ethanolamine (see e.g. Koutsopoulos and Dalas, 2000; Wang et al, 2010)
and/or
an inorganic base, such as but not limited to NaOH, KOH, $NH_3$, $NH_4OH$, $NaHCO_3$, (see e.g. Meyer and Eanes, 1978; Lu, 2005; Yuan et al., 2002)

In one embodiment, the method of the present invention comprises the further step of (6) adding lipid(s) and/or lipid-conjugated molecule(s) and/or further membrane-forming substances to form a lipid bilayer or lipid membrane.

Preferably, the lipid(s) are selected from 1,2-dioleoyl-3-trimethylammonium-propane (DOTAP), 1,2-dioleoyl-sn-glycero-3-phosphocholine (DOPC), phospholipids, sphingolipids.

Preferably, the lipid-conjugated molecule(s) are selected from cholesterol, collagen, fatty acids, protamine, DNA, PEGylated lipid(s), dye conjugated lipid(s).

The present invention provides a nanoparticle obtained by the method of the present invention.

In one embodiment, the nanoparticles obtained by the method of the present invention are mesoporous nanoparticles.

In one embodiment, the nanoparticles obtained by the method of the present invention are amorphous mesoporous nanoparticles.

In one embodiment, the nanoparticles obtained by the method of the present invention are therapeutically active nanoparticles.

Pharmaceutical Compositions

The present invention provides a pharmaceutical composition, comprising (i) at least one nanoparticle of the present invention and/or at least one nanoparticle obtained by the method of the present invention, (ii) optionally, pharmaceutically acceptable carrier(s) and/or excipients.

In one embodiment, the pharmaceutical composition is an injectable formulation.

In one embodiment, the pharmaceutical composition is pressable to pellets, injectable as a gel, a patch, an inhaler, a suppository, injectable as solution, an infusion, or can be applied as additive to crèmes and emulsions, or is a liquid oral application.

Uses of the Nanoparticles as Drug Delivery Systems and Further Medical Uses

The present invention provides the use of
a nanoparticle of the present invention, or
a nanoparticle obtained by the method of the present invention,
as drug delivery system.

Preferably, the drug delivery system is with controlled release. In this preferred embodiment the nanoparticle comprises a lipid membrane.

The present invention provides
the nanoparticle of the present invention, or
the nanoparticle obtained by the method of the present invention, or
the pharmaceutical composition of the present invention for use as a medicament.

The present invention provides
the nanoparticle of the present invention, or
the nanoparticle obtained by the method of the present invention, or
the pharmaceutical composition of the present invention for use as
drug delivery system,
preferably with controlled release,
for bone cement or bone implant or teeth cement, for teeth or medical implants,
preferably as drug reservoir (such as for antibiotics, anti-inflammatories, peptides, proteins, antibodies, vaccines, genes, chemotherapeutics, RNA),
for coatings of medical implants,
preferably as drug reservoir (such as for antibiotics, anti-inflammatories, peptides, proteins, antibodies, vaccines, genes, chemotherapeutics, RNA),
preferably for stents, bone orthopedic replacements, sutures,
bone material,
such as in orthopedic applications,
carrier or delivery system with or without taste masking, such as for tablet applications,
chemotherapeutics.

The present invention provides
the nanoparticle of the present invention, or
the nanoparticle obtained by the method of the present invention, or
the pharmaceutical composition of the present invention for use in the diagnosis and/or treatment of cancer.

Preferably, the nanoparticle comprises chemotherapeutic agent(s).

Preferably, epithelial and/or mesenchymal cancerous cells are targeted and/or affected and/or killed.

In a preferred embodiment, the nanoparticles with/or without a chemotherapeutic agent(s) and/or further compound(s) are released in the cancerous cells, preferably from the endosome into the cytosol and nucleus.

Further Uses of the Nanoparticles

The present invention provides the use of
a nanoparticle of the present invention, or
a nanoparticle obtained by the method of the present invention,
as fertilizer, preferably as phosphate source in fertilizer.

The present invention provides the use of
a nanoparticle of the present invention, or
a nanoparticle obtained by the method of the present invention,
as absorber for metal ions from wastewater and/or water.

The metal ions are e. g. copper, nickel, cobalt, manganese, iron, cobalt, zinc, cadmium, mercury, and/or lead.

Methods of Diagnosis and/or Treatment

The present invention provides a method for the diagnosis and/or treatment of cancer, comprising the step of
administering to a subject in need thereof a therapeutically effective amount of
a nanoparticle of the present invention, or
a nanoparticle obtained by the method of the present invention, or
a pharmaceutical composition of the present invention.

Preferably, the nanoparticle comprises chemotherapeutic agent(s).

Preferably, epithelial and/or mesenchymal cancerous cells are targeted and/or affected and/or killed.

In a preferred embodiment, the nanoparticles with/or without a chemotherapeutic agent(s) and/or further compound(s) are released in the cancerous cells, preferably from the endosome into the cytosol and nucleus.

The present invention provides a drug delivery system, preferably with controlled release, comprising
- a nanoparticle of the present invention,
- a nanoparticle obtained by the method of the present invention, or
- a pharmaceutical composition of the present invention.

The present invention provides a bone cement or bone implant or teeth cement or a teeth implant or a drug reservoir/delivery system for bone or teeth cement or a teeth implant, comprising
- a nanoparticle of the present invention,
- a nanoparticle obtained by the method of the present invention, or
- a pharmaceutical composition of the present invention.

The drug reservoir comprises e.g. antibiotics, anti-inflammatories, peptides, proteins, antibodies, vaccines, genes, chemotherapeutics, RNA.

The present invention provides a coating of medical implants (e.g. stents) or a drug reservoir/delivery system for coating of medical implants, comprising
- a nanoparticle of the present invention,
- a nanoparticle obtained by the method of the present invention, or
- a pharmaceutical composition of the present invention.

The drug reservoir comprises e.g. antibiotics, anti-inflammatories, peptides, proteins, antibodies, vaccines, genes, chemotherapeutics, RNA.

The present invention provides a bone material, comprising
- a nanoparticle of the present invention,
- a nanoparticle obtained by the method of the present invention, or
- a pharmaceutical composition of the present invention,
such as in orthopedic applications.

The present invention provides a carrier or delivery system with or without taste masking, comprising
- a nanoparticle of the present invention,
- a nanoparticle obtained by the method of the present invention, or
- a pharmaceutical composition of the present invention,
such as for tablet applications.

Further Description of Preferred Embodiments

Abstract

For cancer therapy applications nanoparticles are usually designed as carrier systems loaded with toxic drugs that act upon being released at the target site. Here, we present a radically novel concept based on hybrid mesoporous calcium phosphate-citrate nanoparticles that are safe carrier and efficient chemotherapeutic agent in one without the need for additional drugs. Cell uptake of these particles is mediated via a lipid coating that further serves as capping mechanism, preventing premature release of additional cargo molecules loaded into the particles such as labeling dyes or additional drugs. Importantly, in the late endosome the calcium phosphate-citrate nanoparticles are dissolved by the prevailing acidic pH and endosomal release can be induced by small amounts of the additive cetyltrimethylammonium chloride, which we load into the particles as an on-board trigger that is released upon particle dissolution. While calcium phosphate-citrate nanoparticles are not toxic before endosomal release, epithelial cancer cells are killed shortly upon release of the dissolved particles. Mesenchymal cancer cells, which are notoriously difficult to treat with conventional chemotherapeutics, were efficiently killed at even lower calcium phosphate-citrate nanoparticle concentrations than epithelial cells, whereas no significant cell death could be observed for the cell line MCF 10A, which is derived from non-tumorigenic tissue. Thus, calcium phosphate-citrate nanoparticles offer great potential as chemotherapeutic agent with selective, tunable toxicity towards cancer cells, showing no premature release of toxic substances and leaving no toxic residues behind.

Conventional chemotherapeutics lead to severe side effects since toxic substances are usually administered systemically to the patient at high dosage. In recent years strategies have been developed to encapsulate chemotherapeutics and to deliver them efficiently and selectively to the target tissue (Torchilin 2014) However, these concepts still rely on transport of toxic substances, and any lack of efficient targeting, premature leakage or residues of those substances can lead to serious side effects. Here, we present a radically new concept based on colloidal mesoporous hybrid calcium phosphate-citrate nanoparticles that efficiently kill cancer cells without encapsulation of toxic substances. A dense lipid coating facilitates their cell uptake and small amounts of the additive cetyltrimethylammonium chloride allow for efficient endosomal escape. Remarkably, the particles are neither toxic before endosomal release nor after their degradation. We also show that calcium phosphate-citrate nanoparticles affect mesenchymal cancer cells even more than epithelial cancer cells. With this property, they belong to the very few substances that are selectively toxic to mesenchymal cells—an important feature to address metastases (Coley 2008).

Results

Hydroxyapatite ($Ca_{10}(PO_4)_6(OH)_2$), the main inorganic component of bone and teeth, has recently been discussed as a new promising platform for advanced drug delivery applications due to its high biocompatibility and non-toxicity (Iafisco et al., 2009; Dorozhkin and Epple, 2002; Palmer et al., 2008). It is biodegradable (Arcos and Vallet-Regi, 2013) and thus overcomes the challenge of finding a material that has no toxic side effects. For this reason porous apatite loaded with docetaxel (Chen et al., 2014; Ding et al., 2015), silybin (Chen et al., 2015), ibuprofen (Zhao et al., 2012) and doxorubicin (Rodriguez-Ruiz et al., 2013) has been used to deliver these drugs to cells despite its moderate surface area of 315 $m^2$ $g^{-1}$ at maximum (Chen et al., 2014). Co-precipitation of $Ca^{2+}$- and $PO_4^{3-}$-ions with gemcitabine, siRNA, or proteins (Li et al., 2012; Zhang et al., 2013) has also been shown as an method to deliver drugs employing apatite due to its biocompatibility. However, the co-precipitated apatite has been reported to have toxic effects once it is in cells at high concentrations.

Rod-like, non-porous apatite particles have been shown to induce cell death of gastric cancer cells, cervical adenocarcinoma epithelial cells and hepatoma cells, whereas no cell death was observed for normal human hepatocyte cells at concentrations higher than 125 µg $mL^{-1}$ (Tang et al., 2014). Additionally, the impact of particle shape (Zhao et al., 2013-a) and synthesis conditions on the toxic effects of apatite have been investigated (Motskin et al., 2009). The toxicity of apatite particles can be attributed to a sudden release of high amounts of calcium within the small volume of a cell whereas a slow increase by freely diffusing calcium can be regulated by the cells and does not affect them (Orrenius 2003). Based on these findings, hydroxyapatite appears to be an attractive biocompatible and biodegradable chemotherapeutic agent that is toxic only once it enters the cell and is released from the endosome. However, to date this promising potential could not yet be realized since the required toxic concentrations of known apatite particles were too high for pharmaceutical applications—possibly due to poor dissolution efficiency of the apatite and thus slow release of $Ca^{2+}$-ions.

In order to ensure efficient dissolution of the particles in the acidic endosome, we developed the novel concept of hybrid mesoporous calcium phosphate-citrate nanoparticles. We synthesized calcium phosphate-citrate nanoparticles by reacting $Ca^{2+}$- and $PO_4^{3-}$-ions with citric acid at a molar ratio of 5:3:5. Citric acid complexes calcium ions (Xie et al., 2010; Hu et al., 2010) and thus has an important role in respect to the reaction kinetics for the formation of calcium phosphates (Davies et al., 2014; Xie et al., 2010). The precipitation is induced by rapid pH change upon addition of triethanolamine and formation of a mesoporous structure is achieved by addition of the surfactant templates cetyltrimethylammonium chloride and Pluronic F127. Extraction of the surfactant templates yielded the desired mesoporous hybrid calcium phosphate-citrate nanoparticles as depicted in FIG. 1a-c. The successful synthesis of amorphous calcium phosphate-citrate particles was verified by IR-measurements: The IR-spectrum of calcium phosphate-citrate nanoparticles, as shown in FIG. 2, resembles that of crystalline calcium phosphate. It also shows two strong additional vibrations at 1414 $cm^{-1}$ and 1590 $cm^{-1}$ that are attributed to the symmetrical- and the anti-symmetrical stretching modes of $COO^-$ groups from citric acid incorporated into the structure (Socrates 2001; Nakamoto 2009). The incorporation of citric acid was further confirmed by solid state (ss)-NMR spectroscopy (FIG. 3a-c) and determined to be about 20 wt % using thermogravimetric analysis (FIG. 11). Energy dispersive X-ray and inductively coupled plasma methods yielded an atomic ratio Ca:P of 1.61. Without further filtration, the particles showed a narrow size distribution with a hydrodynamic radius of 220 nm in ethanolic solution as measured by dynamic light scattering (FIG. 1d). Electron microscopy images showed particles of about 50 nm; taken together with the light scattering data these results show that some weak aggregation appears to operate in solution (FIG. 1a-c). The size of 50 nm renders the particles perfectly suited for cellular uptake. The porosity of the obtained particles was analyzed with nitrogen sorption measurements. As shown in FIG. 4a we observed a typical type IV isotherm, which is characteristic of mesoporous systems (Sing 1985). The particles feature an extraordinary maximum BET surface area of 900 $m^2\ g^{-1}$, a very narrow pore size distribution with a maximum at 4.5 nm (FIG. 4b), and a cumulative pore volume of 1.0 $cm^3\ g^{-1}$. These remarkable characteristics are very similar to the well-established mesoporous silica particles (Moeller et al., 2007; Slowing et al., 2008). The surface area is almost three times larger than reported before for calcium phosphate based materials.

In contrast, the prior art, in particular Mitsionis et al. (2010), describes only crystalline calcium phosphate ceramic particles and nanoparticles, which can form agglomerates or aggregates having textural pores in the spaces between the agglomerates or aggregates of the particles in the dried state. Said inter-aggregate textural pores are different from the internal mesopores of the nanoparticles of the present invention. Additionally, the calcium phosphate ceramics are not colloidally stable. The calcium phosphate ceramics do not contain citric acid incorporated into the structure of calcium phosphate.

Next, we studied cellular uptake of the newly synthesized calcium phosphate-citrate nanoparticles. Notably, we could not detect any cellular uptake of the bare as-synthesized and extracted calcium phosphate-citrate particles. In analogy to lipid calcium phosphate (LCP) particles (Zhang et al., 2013) that are taken up by cells due to their lipid coating, we sought to enhance particle uptake with a lipid bilayer. We formed a lipid coating consisting of 1,2-dioleoyl-3-trimethylammonium-propane (DOTAP) and 1,2-dioleoyl-sn-glycero-3-phosphocholine (DOPC) around the particles employing the solvent exchange method (Cauda et al., 2010). Successful formation of the lipid coating resulted in a drastic increase in Zeta potential (FIG. 1d, inset) from −5 mV to +20 mV at pH 7.4, due to the positively charged DOTAP (Lopez-Macipe et al., 1998). To assess the integrity of the lipid coating, we loaded the particles with the non membrane-permeable fluorescent dye calcein and measured its release over a time period of 24 h in a two-compartment cuvette experiment (FIG. 6). We could not detect any significant premature release (<1%), thus confirming a successful lipid coating. Acidification by addition of 0.1 M HCl dissolved the particles and led to a dramatic increase in released fluorescent dye, as measured after neutralization to pH 7.4 (FIG. 7).

We then investigated the uptake of lipid-coated calcium phosphate-citrate nanoparticles loaded with calcein by HeLa cells. As depicted in FIG. 8, the lipid-coated calcium phosphate-citrate nanoparticles were successfully internalized by the cells. We monitored the cells over a period of several days. While the internalized particles were still very close to the cell membrane after 24 h, they were close to the nucleus after 48 h and no further development could be observed during the following days. Compared to other nanoparticles such as mesoporous silica, endocytosis of calcium phosphate-citrate nanoparticles is rather slow. We attribute this to the presence of citric acid and phosphate ions from the lipid-coated calcium phosphate-citrate nanoparticles forming a McIlvaine's buffer (McIlvaine 1921) with high buffering capacity that slows down the proton pump-driven process. We could not detect any impact of the internalized calcium phosphate-citrate nanoparticles on cell viability up to very high particle concentrations, nor could we observe any intracellular release from purely lipid-coated calcium phosphate-citrate nanoparticles loaded with calcein (FIG. 9a-h). These particles were still caught in the endosome thus preventing release of calcein or toxic calcium amounts.

To enable endosomal release, we loaded the particles with a small amount of cetyltrimethylammonium chloride (CTAC, 6.25 µg, 19.5 nmol). CTAC is a positively charged surfactant that can destabilize lipid membranes. While adsorbed in the particle, its attraction to the negatively charged particle prevents leakage and destabilization of the lipid coating of the particles. However, once the endosomal pH turns acidic (Sorkin et al., 2002; Gruenberg et al., 2001; Matsuo et al., 2004), the particle dissolves and releases the small amount of CTAC molecules. The dissolved particles strongly increase the ionic concentration inside the endosome thus causing an influx of water. This process leads to the enlargement of the endosome, and eventually to its rupture assisted by the destabilizing effect of CTAC (Varkouhi et al., 2011; Behr 1997; Sonawane et al., 2003; Slowing et al., 2006). When incubating HeLa cells with lipid-coated calcium phosphate-citrate nanoparticles loaded with calcein and CTAC, we could observe a sudden release of calcein in the cells within 72 h, quickly followed by cell death. We attribute this observation to a rupture of the endosome containing the dissolved particle and its cargo calcein. The subsequent release of the endosomal content leads to a sudden increase of intracellular calcium levels that is suggested to induce the observed apoptosis (Orrenius 2003). We propose that the unique efficient calcium-releasing behavior of our novel calcium phosphate-citrate nanoparticles is based on their amorphous nature and their extremely thin walls with very high surface area, hence creating conditions for drastically enhanced dissolution kinetics in the endosome in comparison with established calcium phosphate particles.

In order to test the toxicity of the remaining material on neighboring cells, we incubated dissolved calcium phosphate-citrate nanoparticles with HeLa cells, including those loaded with calcein and CTAC. We did not detect any significant loss in viability (FIG. 13). The toxic effect of calcium phosphate-citrate nanoparticles loaded with calcein and CTAC seems to be limited to sudden intracellular release of high amounts of calcium upon endosomal rupture, thus preventing undesired further damage to neighboring cells.

The above results on HeLa cells suggest very promising properties of calcium phosphate-citrate nanoparticles when applied as chemotherapeutic agents that avoid highly toxic substances. We next studied their effect on several other cell lines to assess their general performance. For this purpose we chose four cancerous mesenchymal cell lines (HeLa, H1299, MDA-MB-231, LLC), three cancerous epithelial cell lines (BT-474, MCF7, HuH7), and one epithelial cell line derived from non-tumorigenic tissue (MCF 10A). All tested cell lines internalized lipid-coated calcium phosphate-citrate nanoparticles. We then performed MTT tests to measure cell viability after 72 h. Neither uncoated calcium phosphate-citrate nanoparticles nor lipid-coated calcium phosphate-citrate nanoparticles without CTAC showed significant toxicity up to concentrations of 100 µg mL$^{-1}$ in any of the cell lines (FIG. 9$a$-$h$). However, viability of all cancerous cell lines was strongly decreased after incubation with lipid-coated calcium phosphate-citrate nanoparticles loaded with CTAC—even at concentrations of less than 30 µg mL$^{-1}$. (FIG. 9$i$-$j$, Table 2) Strikingly, the non-cancerous cell line MCF 10A was not affected significantly by the particles up to concentrations of 100 µg mL$^{-1}$ (FIG. 9$d$). These results suggest a strong selectivity in the toxic effect of calcium phosphate-citrate nanoparticles, thus demonstrating their potential as chemotherapeutic agents.

We further determined the IC$_{50}$ values for all tested cell lines. They are depicted in FIG. 9$j$ and exhibited a large difference between mesenchymal and epithelial cells. Mesenchymal cells are affected much stronger than epithelial cells. This allows us to selectively treat mesenchymal cells while keeping epithelial cells alive, simply via adjustment of the concentration. With these unusual properties, calcium phosphate-citrate nanoparticles belong to the small group of substances that can be used to selectively treat mesenchymal cells, similarly to salinomycin (Kopp et al., 2014; Gupta et al., 2009). We suggest that the enhanced sensitivity of mesenchymal cells toward intracellular calcium levels is an important reason for the strong toxic effect of calcium phosphate-citrate nanoparticles.

TABLE 2

IC$_{50}$ values of investigated cell lines.

| epithelial cell lines | | mesenchymal cell lines | |
| --- | --- | --- | --- |
| cell line | IC$_{50}$ (µg mL$^{-1}$) | cell line | IC$_{50}$ (µg mL$^{-1}$) |
| BT-474 | 30.0 | H1299 | 8.2 |
| MCF7 | 18.5 | HeLa | 8.0 |
| HuH7 | 14.0 | MDA-MB-231 | 4.4 |
| MCF 10A | — | LLC | 4.0 |

Based on the findings reported here, we believe that the novel mesoporous calcium phosphate-citrate nanoparticles show intriguing potential as chemotherapeutic agents with drastically reduced side effects. As a key feature, they do not contain intrinsically toxic substances. Their tunable uptake behavior, adjustable toxicity and selectivity towards different cancer cell lines, biocompatibility and low cost makes these unusual nanoparticles highly promising candidates for applications in chemotherapy.

Our invention exhibits combined properties for the effective treatment of epithelial and mesenchymal cancer cells. We achieve this with a new mesoporous transport system, which consists of biogenic components. The particles dissolve in the acidic endosome and open it. Additionally, we can tune the endosomal escape with an additive and optimize this effect as intended. After the endosomal escape, the investigated cancerous cells die, whereas the healthy cells are barely damaged. Our invention is effective against cancerous epithelial cell lines to a similar extent as the known cytotoxic agent doxorubicin. Yet our nanoparticles prove an increased effectivity against mesenchymal cancerous cell lines and therefore join the small list of active substances for the treatment of these tumor cells. By contrast, the nanoparticles that were not taken up by cells were identified as biocompatible substances and showed no damaging effects. In summary, we are able to tune the particles in such a manner that we can choose which specific cells (mesenchymal, epithelial or healthy) we wish to treat.

With our system we can deliver additional drugs and use well-known targeting methods, which could ultimately enable a personalized chemotherapy. To date there are reservations against injecting stable nanoparticles into the human body. We suggest that these reservations will disappear because our new nanoparticle system is comprised of biocompatible components and can dissolve after endocytosis.

Because of the significant chemical similarity of the calcium phosphare-citrate nanoparticles of the present invention with bone and teeth material (Pekounov and Petrov, 2008), there are further medical applications in addition to chemotherapeutic treatments:

(i) The nanoparticles can be loaded with drug(s) (such as antibiotics) and be used as bone- or teeth-cement or in bone- or teeth-cement. Thus, the drug(s) (such as antibiotics) will be released over a longer time period, which overcomes the challenge of the so-called burst release observed with today's established bone cement methods. The significant advantage of our material is illustrated by new results that discuss the involvement of citric acid during bone regeneration (Davies et al., 2014). Thus, the precursors for corporeal bone synthesis are united within our nanoparticles and thereby directly accessible at the site of synthesis. We show that our nanoparticles, if not protected with a lipid membrane, undergo a phase transition from the amorphous phase into crystalline bone material within 24 hours in simulated body fluid.

(ii) A further application is as a tasteless transport system for administration of tablets (see DE 10 2004 012 273.3). Water soluble and insoluble drugs can be loaded into the pores of our particles and can be encapsulated. Pressed to a tablet the particles will only dissolve in gastric acid where the drug then will be released.

(iii) Furthermore, crystalline calcium phosphate nanoparticles were investigated as efficient phosphate source in fertilizers (Liu et al., 2014). Our invention basically differs from known phosphate fertilizers. Additionally, a buffer system is formed with the incorporated citrate that regulates the pH-value of the soil.

(iv) The nanoparticles of the present invention can further be used as absorbent for metal ions from wastewater.

Variation of Chemical Structure

Our experiments were performed with calcium phosphate-citrate particles with the stated synthesis procedure and a composition of "$Ca_5(PO_4)_3OH$"•citrate. It is possible to chemically vary the synthesis route, to obtain nanoparticles that exhibit similar properties like the nanoparticles as described in the examples. The following parameters can be varied in the synthesis of the nanoparticles:

Regarding the calcium source $Ca(NO_3)_2 \cdot 4\, H_2O$ the nitrate ions can be exchanged with different anions.

Regarding the phosphate source $(NH_4)H_2PO_4$, the cations can be varied and different phosphate sources such as other $PO_4^{3-}$ salts/acids, including adenosine-triphosphate, -diphosphate, or -monophosphate can be used.

The $OH^-$ ions can be substituted or exchanged with halides or pseudo-halides.

The $PO_4^{3-}$ ions can be substituted with carbonate, sulfate, borate, phosphonate, sulfonate, sulfonamide.

The $Ca^{2+}$ ions can be substituted with different divalent cations such as $Mg^{2+}$, $Ba^{2+}$, $Ti^{2+}$, $Fe^{2+}$, $Zn^{2+}$, $Pt^{2+}$, $Cu^{2+}$, lanthanides (e.g. $Eu^{2+}$).

The ratio of Ca/P is variable.

Citric acid and ethylenglycol can each be exchanged or substituted by other complexing agents.

The base triethanolamine can be exchanged with other bases such as biogenic bases or inorganic bases.

The template for the pore structure can vary in chain length, including longer ones. such as octadecyltrimethylammonium halide(s), and/or shorter ones, such as dodecyltrimethylammonium halide(s). Additionally, other biogenic surfactants and different polymers can be used as templates.

The size of the particles can be varied e.g. 5-5000 nm.

The composition of the lipids can be varied, or due to addition of other polymers such as collagen a different closure mechanism could be realized.

The lipid membrane can be modified by additional lipid-conjugated molecules that present functions at the outer surface of the nanoparticle such as ligands for receptors to cell surfaces, polymers for colloidal stabilization of the particles, dyes for tracking of the particles in cells and tissue, as well as other possible functions.

The following examples and drawings illustrate the present invention without, however, limiting the same thereto.

(a-c) Transmission Electron Microscopy images (scale bars=50 nm). (d) Dynamic-Light-Scattering of calcium phosphate-citrate particles in ethanol and Zeta Potential measurements at pH 7.4 with and without lipid membrane.

Figure 1:
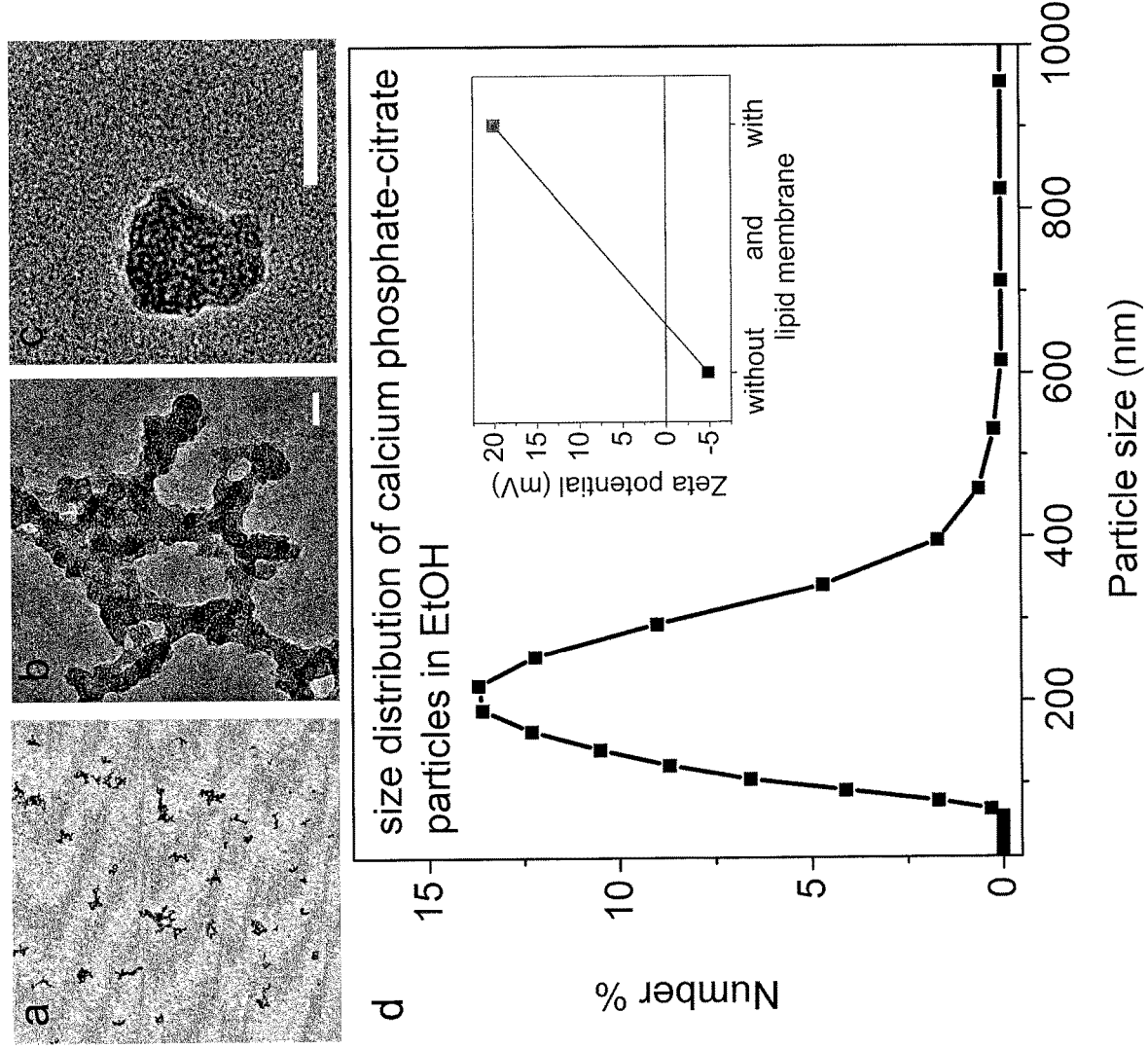
FIG. 1.
Figure 2:
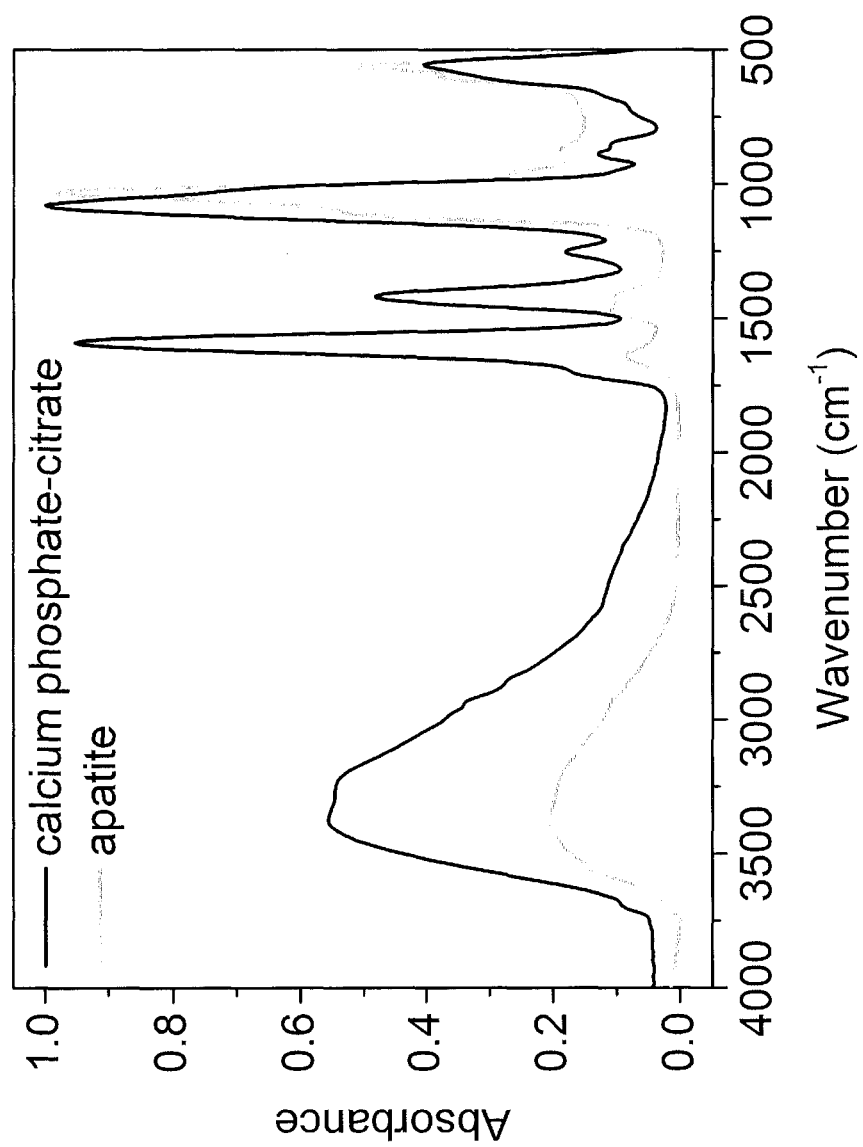

FIG. 2. Infrared Spectroscopy of the Nanoparticles of the Invention.

Calcium phosphate-citrate (black line) nanoparticles with strong C—O vibrational bands at 1590 $cm^{-1}$ and 1400 $cm^{-1}$ that result from the citrate incorporated into the calcium phosphate structure. The phosphate vibration of amorphous calcium phosphate-citrate arises at 1078 $cm^{-1}$. Crystalline apatite (grey line) obviously features weaker C—O bands that result from carbonate containing apatite. The phosphate vibration is shifted to lower wavenumbers at 1040 $cm^{-1}$ due to its crystallinity.

Figure 3:
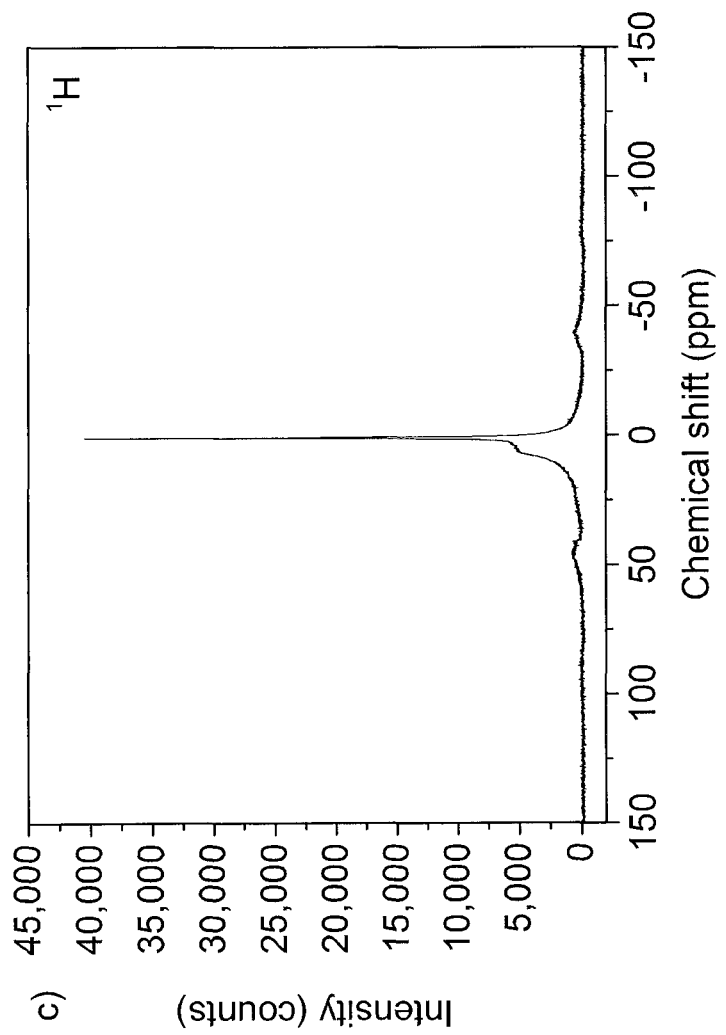

FIG. 3. Solid-state NMR (ssNMR) spectra of Calcium Phosphate-citrate Nanoparticles (a) $^{31}P$ $\{^1H\}$ NMR spectrum, the resonance of $(PO_4)^{3-}$ is located at 1.62 ppm. (b) $^{13}C$ $\{^1H\}$ NMR spectrum, the resonance of structural citrate is located for the primary C-atoms at 179 ppm, for the secondary C-atoms at 44 ppm, and for the tertiary C-atoms at 74 ppm. (c) $^1H$ NMR spectrum, the resonance at 1.14 ppm is assigned to structural O—H. The shoulder results from adsorbed $H_2O$.

Figure 4:
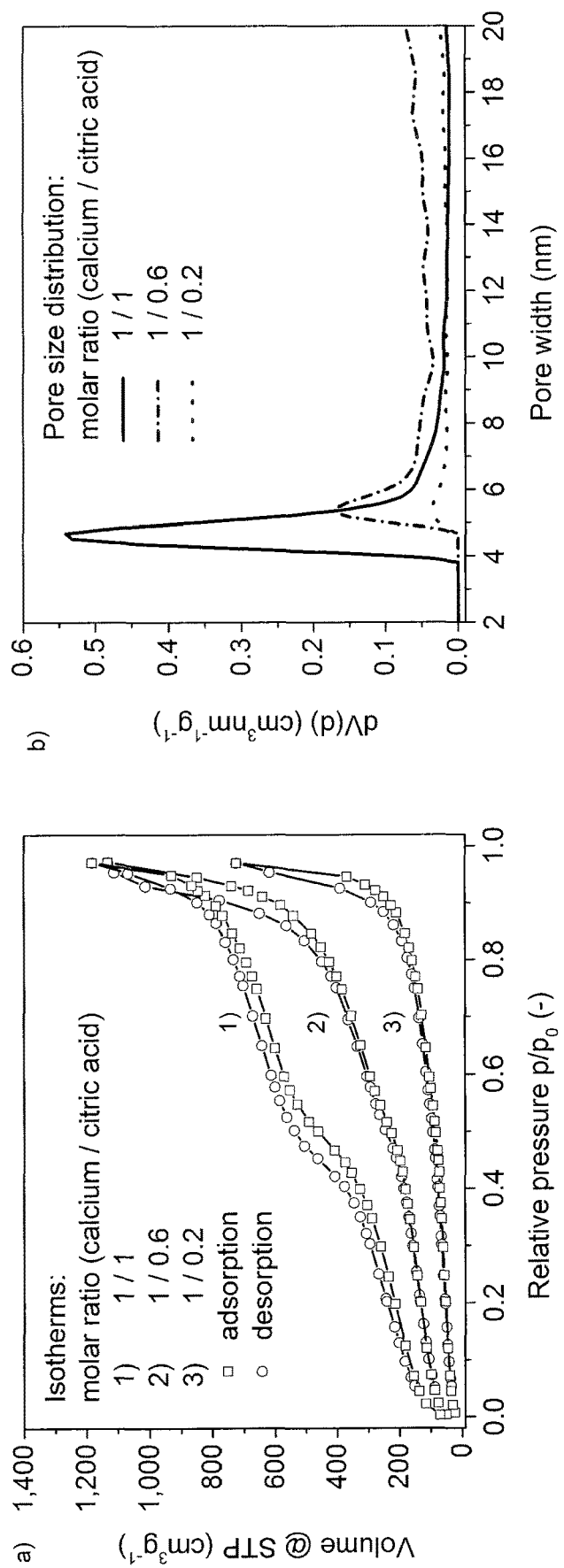

FIG. 4. $N_2$-Sorption isotherms of Calcium Phosphate-citrate nanoparticles (a) Nitrogen sorption in dependence of the citrate concentration with a maximum BET surface area of 900 $m^2/g$, (b) a very narrow pore size distribution with a maximum at 4.5 nm, and a cumulative pore volume of 1.0 $cm^3/g$.

Figure 5:
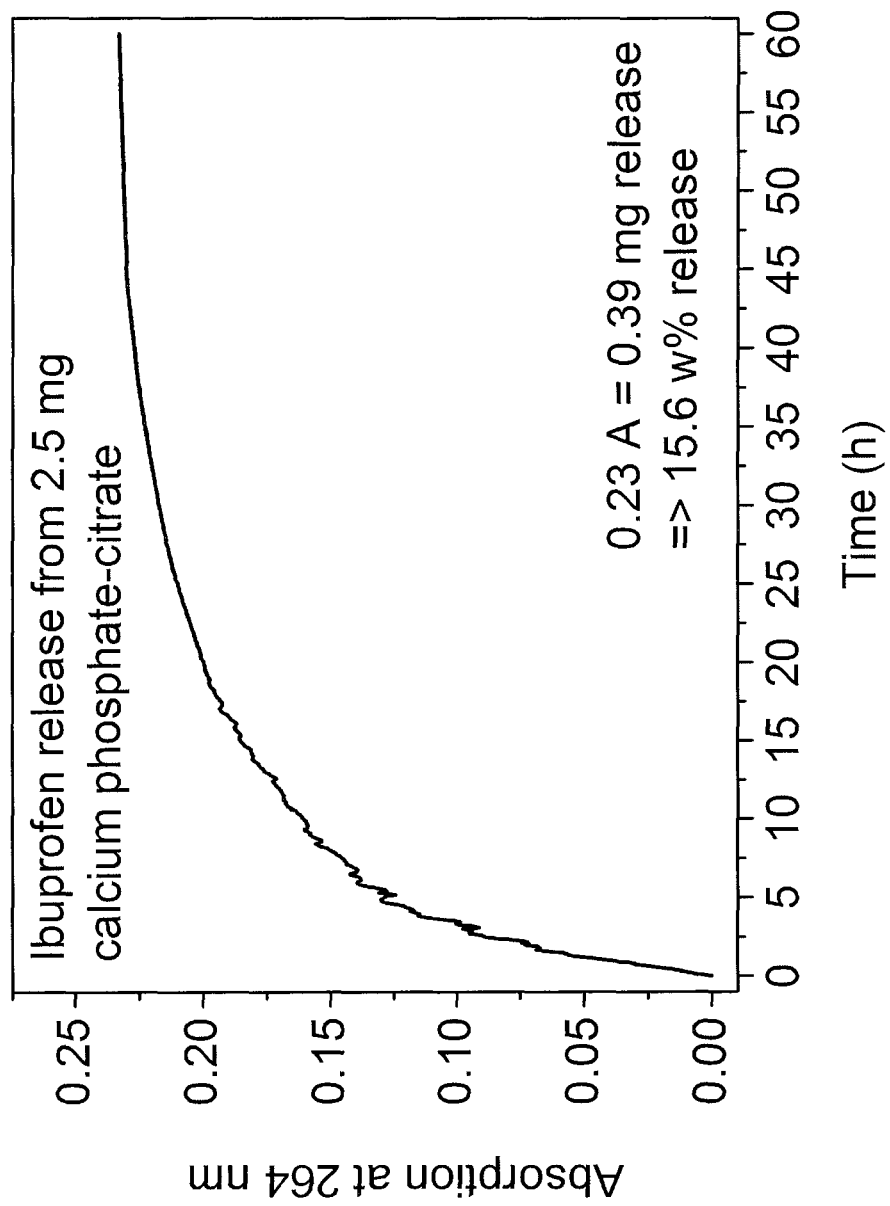

FIG. 5. Drug Release.

UV-Vis measurement of the release kinetics of ibuprofen detecting at 264 nm in simulated body fluid at pH 7.4.

FIG. 6. Cuvette Setup for Measurement of Release from the Nanoparticles.

(a) Loaded nanoparticles are separated from the measuring compartment with a membrane.

(b) After dissolving the particles by addition of acid through an opening in the cap, the drug can diffuse through the membrane and is detected in the cuvette.

Figure 7:
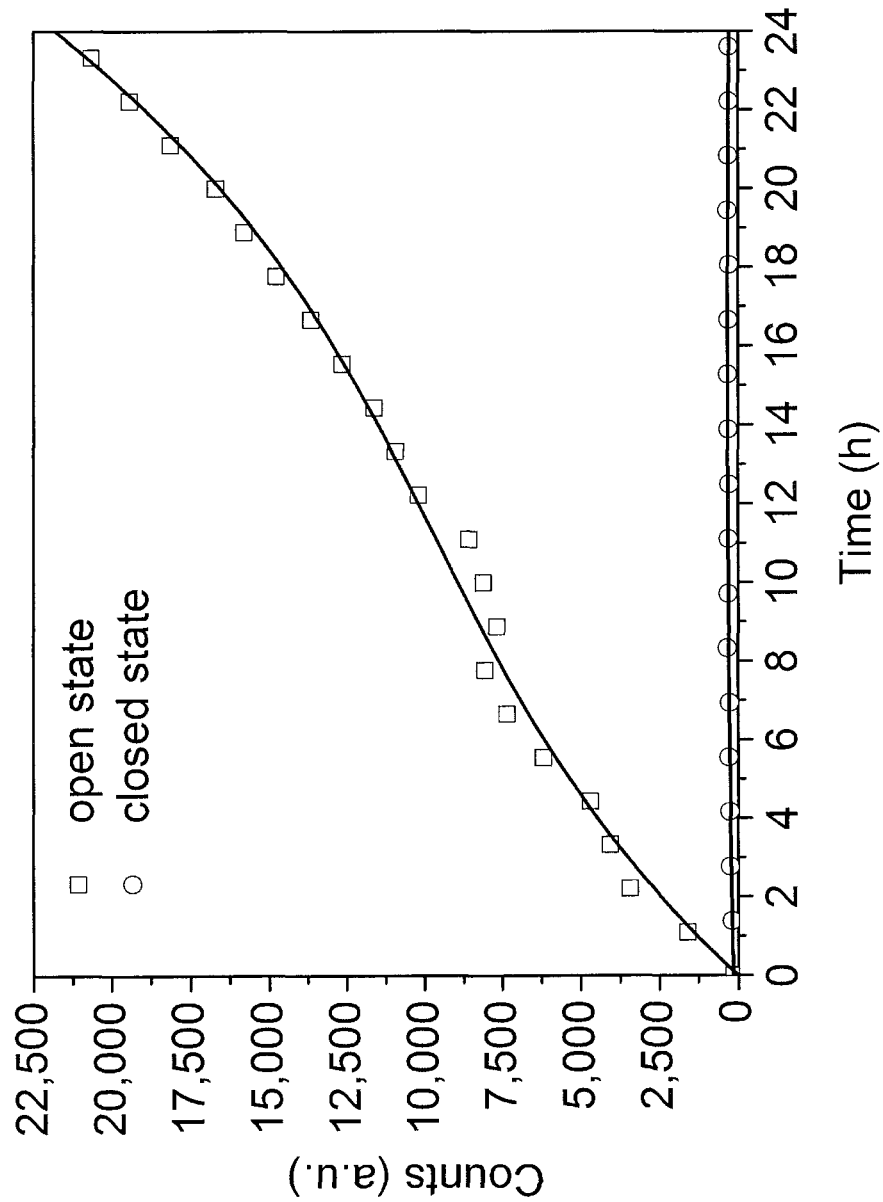

FIG. 7. In vitro release experiment with calcein in simulated body fluid (pH=7.4). The circular dots depict the fluorescence in the measurement cell of closed particles, the squared dots the fluorescence of particles in the open state (excitation=495 nm/emission=512 nm). The particles show no premature release of the dye over a time period of 24 hours. After dissolving the particles by acidification, similar to the pH reduction in the endosome of cells, the release of the dye is enabled.

Figure 8:
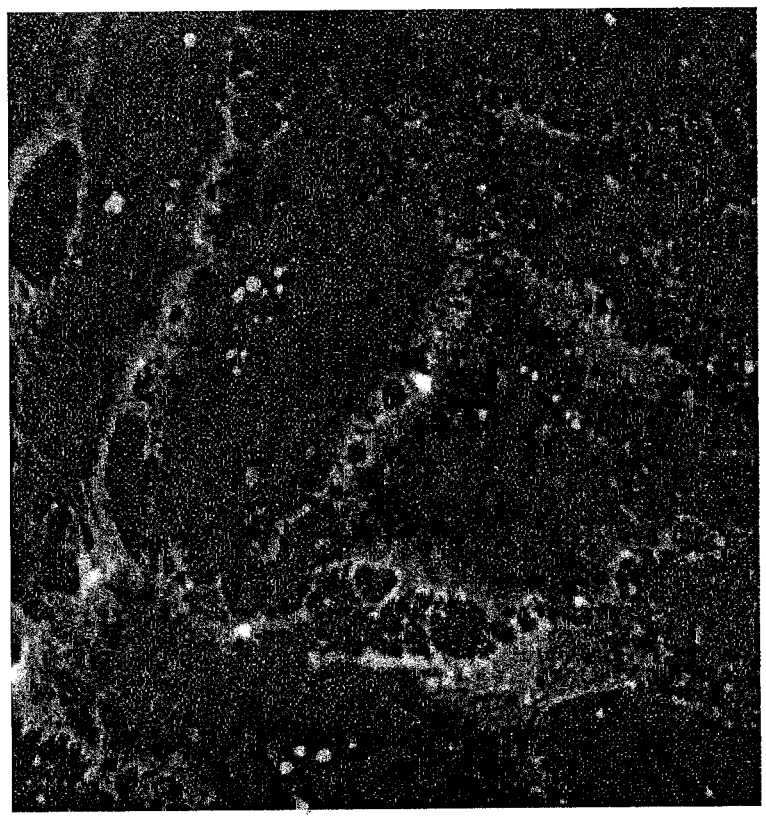

FIG. 8. Spinning-Disc-Microscopy image of calcium phosphate-citrate-lipid particle uptake in HeLa cells 48 hours after treatment. Particles (gray dots) are efficiently taken up by the cells (membrane stained with wheat germ agglutinin (WGA), gray structure).

FIG. 9. Cell Viability of Investigated Cell Lines.

MTT-Assay with readout after 72 hours after treatment.

(a-d) four different epithelial cell lines (BT-474, MCF7, HuH7 and MCF 10A). (f-h) four different mesenchymal cell lines (H1299, HeLa, MDA-MB-231 and LLC). Triangular dots display calcium phosphate-citrate particles, which were not taken up by cells. Circular dots display calcium phosphate-citrate-lipid particles, which were taken up by cells but did not escape from the endosome due to the lack of required additive. Squared dots display calcium phosphate-citrate-lipid particles that were taken up by cells and showed endosomal escape.

(i) $IC_{50}$ plot of all investigated cell lines.

(j) $IC_{50}$ values of the investigated cancerous epithelial (HuH7, MCF7, BT-474), the non-tumorigenic epithelial (MCF 10A, no significant cell death observed and no $IC_{50}$ was calculated), and the cancerous mesenchymal (MDA- MB-231, LLC, H1299, HeLa) cell lines after treatment with lipid-coated calcium phosphate-citrate particles that escape from the endosome. The horizontal lines mark the average $IC_{50}$ values from the same cell line types (long dashes for cancerous epithelial and dots for cancerous mesenchymal cell lines) for comparison of the selectivity of the calcium phosphate-citrate particles FIG. 10. Phase transformation of amorphous calcium phosphate-citrate particles (2 h) into crystalline apatite (96 h) in simulated body fluid; traces are shifted by 500 counts.

Figure 11:
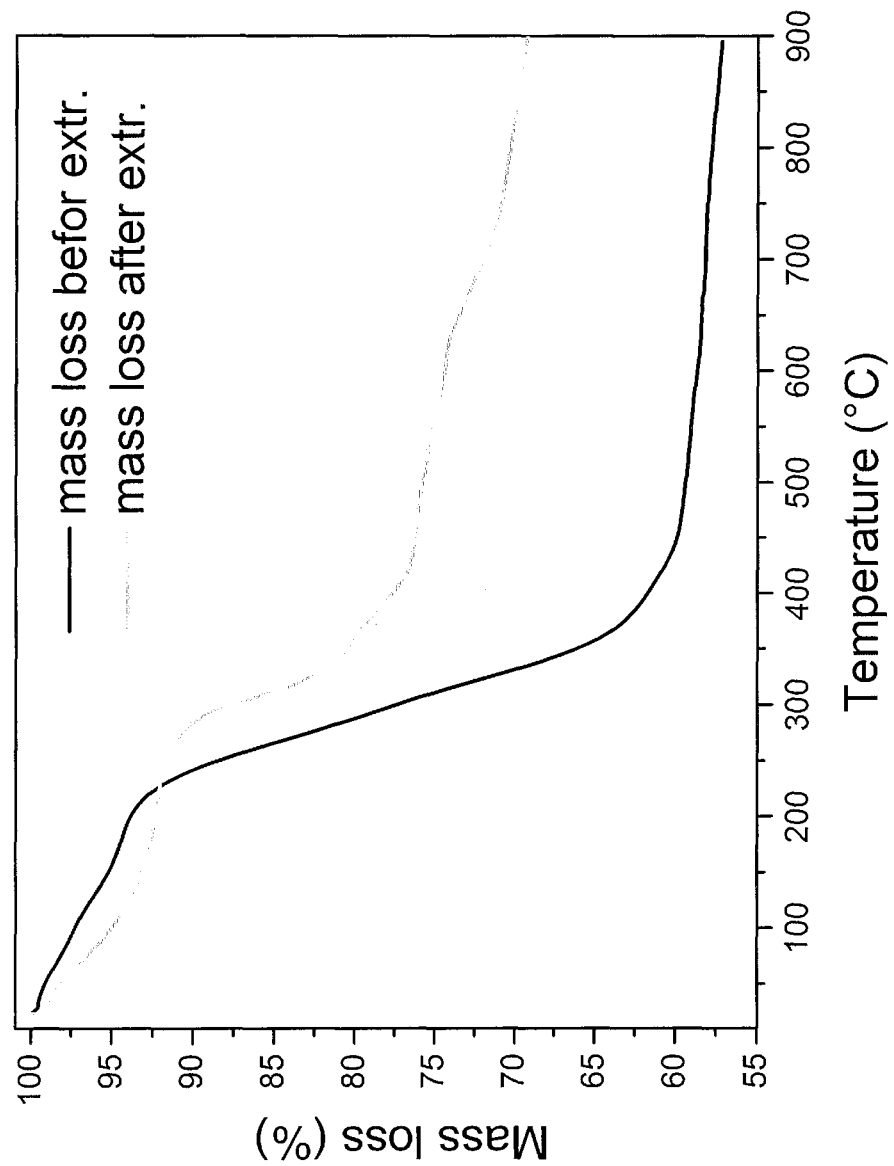

FIG. 11. Thermogravimetric Analysis.

The incorporation of citric acid into the framework of the hybrid calcium phosphate-citrate particles was additionally visualized with TGA measurements. Mass loss of calcium phosphate-citrate particles before (black line) and after (gray line) extraction.

FIG. 12.

Small angle (SAXS) and wide angle (WAXS, inlet) X-Ray scattering of calcium phosphate-citrate particles with Cu-Kα radiation.

FIG. 13.

The previously dissolved particles had no effect on cell viability in HeLa cells up to concentrations of ~100 μg $mL^{-1}$, while the calcium phosphate-citrate-lipid particles induced apoptosis with an $IC_{50}$ of 8.0 μg $mL^{-1}$. Circular dots display previously solved calcium phosphate-citrate-lipid particles. Squared dots display calcium phosphate-citrate-lipid particles that escape from the endosome.

Figure 14:
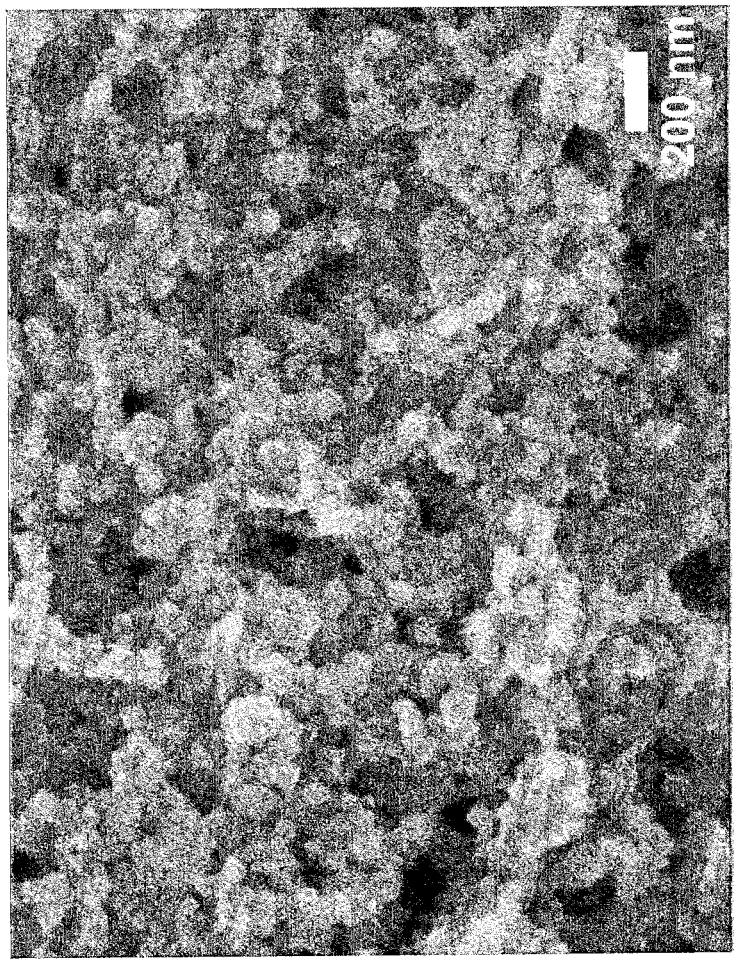

FIG. 14. SEM image of dried calcium phosphate-citrate nanoparticles of the present invention.

The single particles of the present invention exhibit spherical shape at the nanoscale with approximately 50 nm in diameter. Due to the drying process the particles aggregate.

FIG. 15.

(a) Sorption isotherm of calcium phosphate-citrate particles synthesized without adding surfactant template. The particles feature a BET surface area of 500 $m^2/g$, a pore size distribution with a maximum at 11 nm and a corresponding pore volume of 1.0 $cm^3/g$.

(b) Spinning-Disc-Microscopy image of calcium phosphate-citrate-lipid particle synthesized without adding surfactant template uptake in HeLa cells 48 hours after treatment. Particles (gray dots) are efficiently taken up by the cells (membrane stained with wheat germ agglutinin (WGA), gray structure).

FIG. 16.

(a) Dynamic-Light-Scattering of magnesium phosphate-citrate particles in ethanol.

(b) Magnesium phosphate-citrate (black line) nanoparticles with strong C—O vibrational bands at 1622 $cm^{-1}$ and 1420 $cm^{-1}$ that result from the citrate incorporated into the magnesium phosphate structure. The phosphate vibration of amorphous magnesium phosphate-citrate arises at 1081 $cm^{-1}$.

(c) Wide angle X-Ray scattering (WAXS) of magnesium phosphate-citrate particles, obtained with Cu-K$_\alpha$ radiation.

Figure 17:
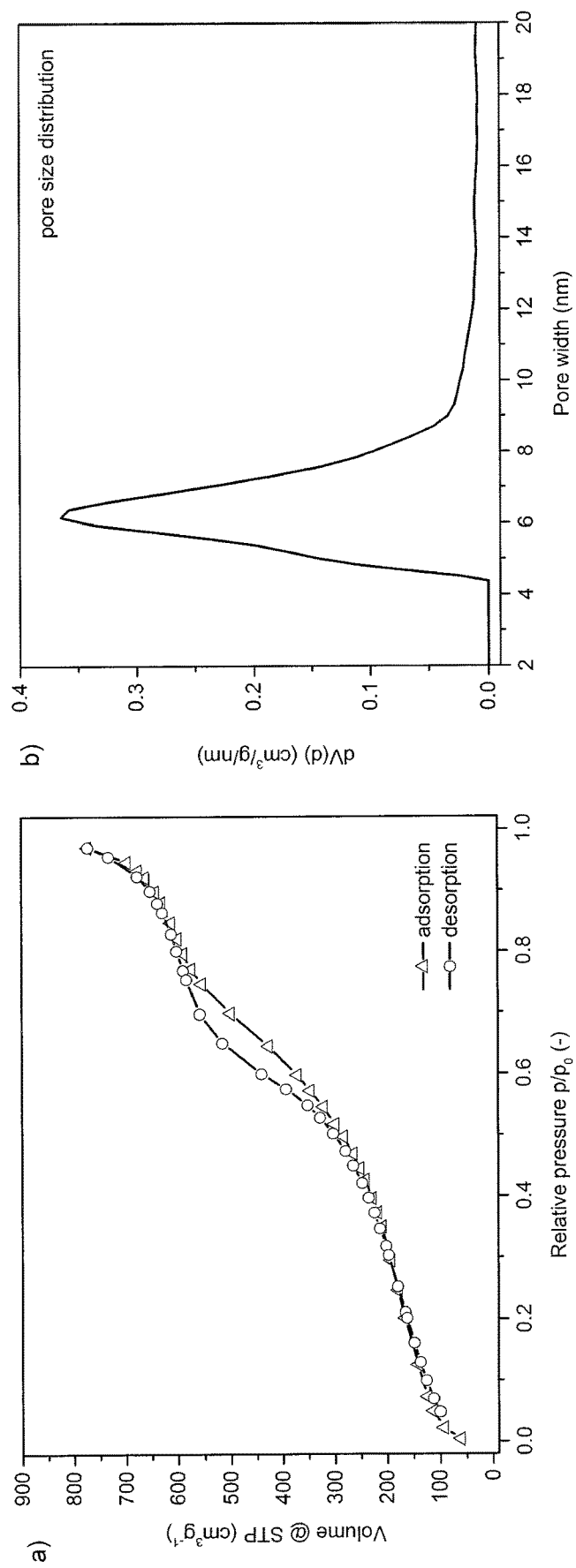

FIG. 17. Nitrogen sorption isotherms of magnesium phosphate-citrate nanoparticles.

(a) Nitrogen sorption isotherm with a BET surface area of 620 $m^2/g$, (b) a narrow pore size distribution with a maximum at 6.2 nm, and a cumulative pore volume of 0.8 $cm^3/g$.

FIG. 18.

(a-c) Scanning Electron Microscopy images of magnesium phosphate-citrate nanoparticles.

(d-f) Transmission Electron Microscopy images of magnesium phosphate-citrate nanoparticles.

Figure 19:
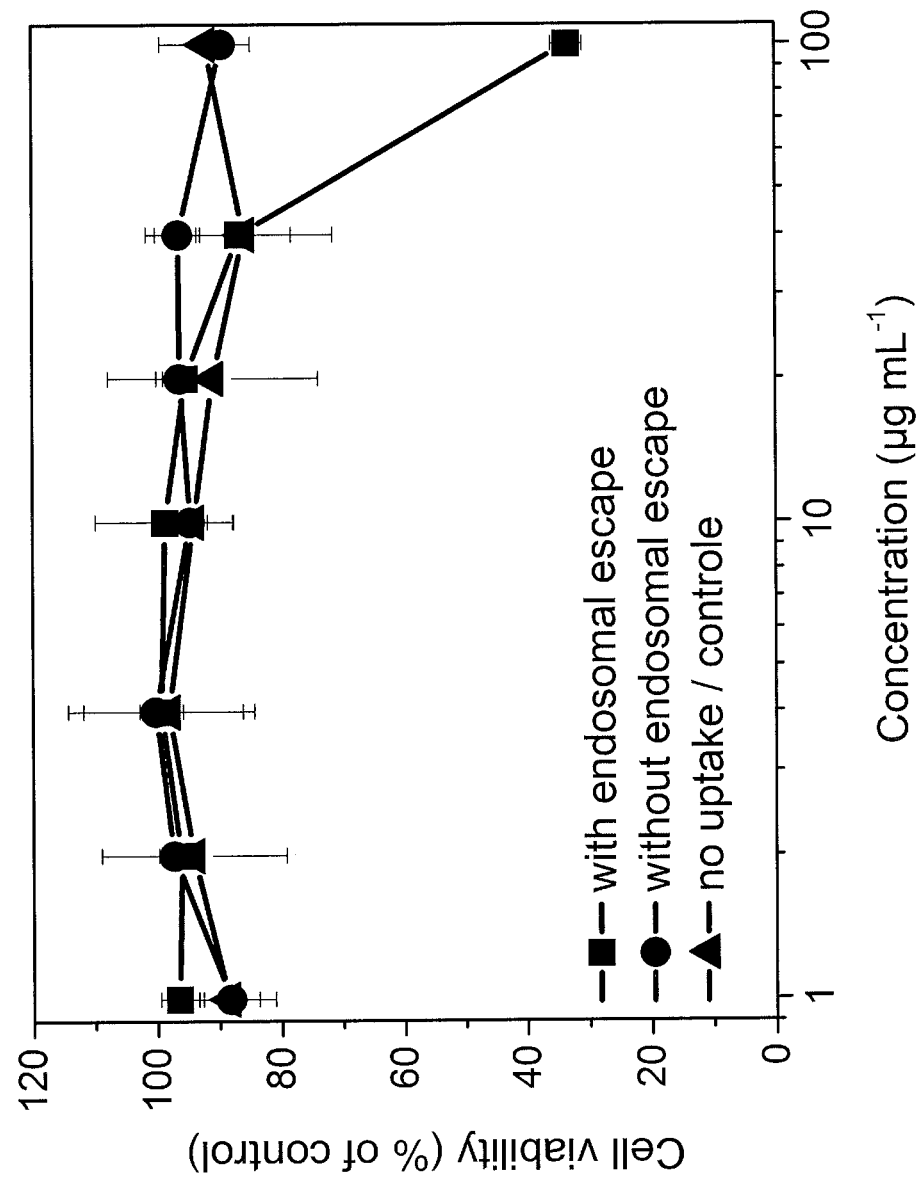
Figure 20:
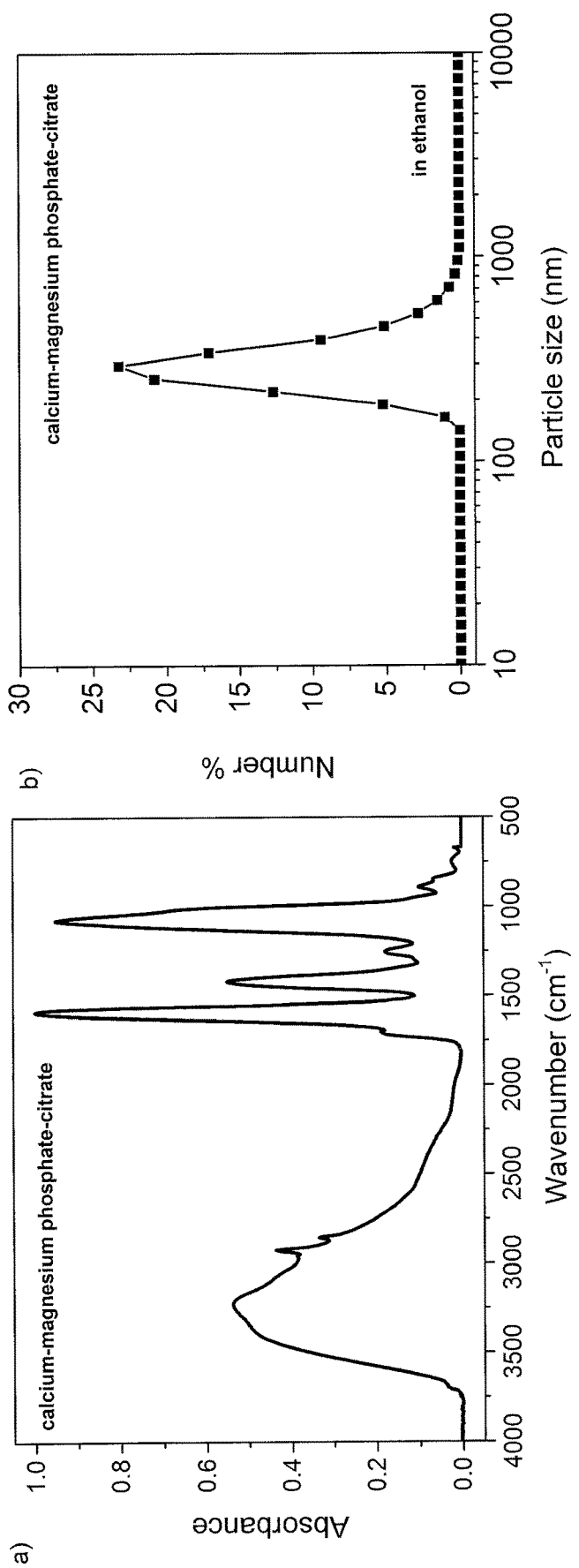
Figure 21:
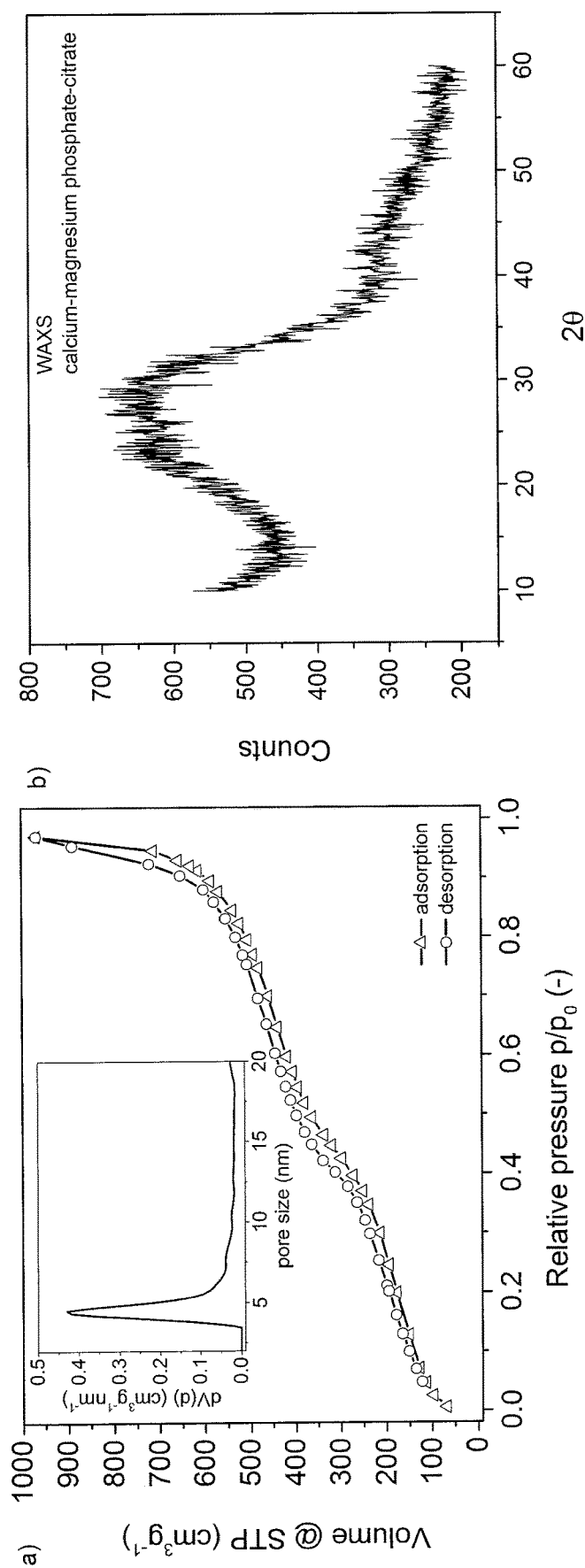

FIG. 19. Cell Viability of HeLa Cell Line towards magnesium phosphate-citrate nanoparticles.

MTT-Assay with readout after 72 hours after treatment.

Triangular dots display magnesium phosphate-citrate particles that were not taken up by cells. Circular dots display magnesium phosphate-citrate-lipid particles that were taken up by cells but did not escape from the endosome due to the lack of required additive. Squared dots display magnesium phosphate-citrate-lipid particles that were taken up by cells and showed endosomal escape.

FIG. 20.

(a) Calcium-magnesium phosphate-citrate (black line) nanoparticles with strong C—O vibrational bands at 1594 $cm^{-1}$ and 1415 $cm^{-1}$ that result from the citrate incorporated into the calcium-magnesium phosphate structure. The phosphate vibration of amorphous calcium-magnesium phosphate-citrate arises at 1078 $cm^{-1}$.

(b) Dynamic-Light-Scattering based pore size distribution of calcium-magnesium phosphate-citrate particles in ethanol.

FIG. 21.

(a) Nitrogen sorption isotherm of calcium-magnesium phosphate-citrate particles with a BET surface area of 740 $m^2/g$, a narrow pore size distribution with a maximum at 4.6 nm, and a cumulative pore volume of 0.66 $cm^3/g$.

(b) Wide angle X-ray scattering (WAXS) of calcium-magnesium phosphate-citrate particles, obtained with Cu-K$_\alpha$ radiation.

FIG. 22.

(a) Scanning Electron Microscopy images of calcium-magnesium phosphate-citrate nanoparticles.

(b) Spinning-Disc-Microscopy image of calcium-magnesium phosphate-citrate-lipid particle uptake in HeLa cells 48 hours after treatment. Particles (gray dots) are efficiently taken up by the cells (membrane stained with wheat germ agglutinin (WGA), gray structure).

EXAMPLES

Example 1 Materials & Methods 1.1 Chemicals:

Calcium nitrate tetrahydrate (AppliChem, 99%), magnesium nitrate hexahydrate (Aldrich, 99%), ammonium dihydrogenphosphate (Alfa Aeser, 99%), citric acid (Aldrich, 99.5%), cetyltrimethylammonium chloride (CTAC, Fluka, 25 wt % in $H_2O$), Pluronic F127 (Aldrich), ethylene glycol (Aldrich, 99.8%), ethanolamine (Aldrich, 99%), triethanolamine (TEA, Aldrich, 98%), ethanol (EtOH, Aldrich, >99.5%), ammonium nitrate (Sigma, 99%), D-(+)-pantothenic acid calcium salt (Sigma, 99%), hydrochloric acid (Sigma, 2 M), dipotassium hydrogen phosphate trihydrate (Sigma, 99%), sodium hydroxide (Sigma, 2 M), simulated body fluid (prepared as described elsewhere, see Kokubo and Takadama, 2006; Sigma, >99%), calcein (CAL, Sigma), 1,2-dioleoyl-3-trimethylammonium-propane (DOTAP, Avanti Polar Lipids), 1,2-dioleoyl-sn-glycero-3-phosphocholine (DOPC, Avanti Polar Lipids), sodium hydroxide (Aldrich, 0.1 M).

All chemicals were used as received without further purification. Doubly distilled water from a Millipore system (Milli-Q Academic A10) was used for all synthesis steps.

1.2 Synthesis of Calcium Phosphate-Citrate Nanoparticles:

The synthesis of the colloidal and spherical calcium phosphate-citrate compound was achieved with an adjusted Pechini process (Pechini 1967; Yang et al., 2011) See also U.S. Pat. No. 3,330,697 A.

In a 50 mL polypropylene reactor citric acid (CA, 240 mg/144 mg/48 mg, 1.25 mmol/0.75 mmol/0.25 mmol), $Ca(NO_3)_2 \cdot 4\ H_2O$ (295 mg, 1.25 mmol) and $(NH_4)H_2PO_4$ (86.3 mg, 0.75 mmol) were dissolved in water (20 mL, 1.11 mmol) to obtain solutions with a Ca:CA molar ratio of 1:1, 1:0.6 and 1:0.2. Then cetyltrimethylammonium chloride (622 mg, 1.94 mmol), Pluronic F-127 (100 mg) and ethylene glycol (7.15 g, 115 mmol) were added under stirring and cooled at 0° C. for 5 minutes. This solution was added under vigorous stirring to triethanolamine (7.15 g, 48 mmol). The suspension was stirred at 500 rpm at room temperature for 10 minutes. Then the suspension was diluted approximately 1:1 with ethanol. The particles were separated by centrifugation at 19,000 rpm (43,146 RCF) for 15 minutes and redispersed in $NH_4NO_3$/EtOH (2 w %, 80 mL). To extract the template, the suspension was heated under reflux conditions at 90° C. for 30 minutes. Then the particles were separated by centrifugation at 19,000 rpm (43,146 RCF) for 10 minutes and redispersed in 80 mL ethanol. The mixture was heated under reflux conditions at 90° C. for 30 minutes. The particles were separated by centrifugation at 19,000 rpm (43,146 RCF) for 10 minutes and redispersed in 20 mL ethanol.

1.3 Synthesis of Crystalline Apatite:

For the synthesis of crystalline apatite D-(+)-pantothenic acid calcium salt (476 mg, 1 mmol) was dissolved in 12 mL water and the pH was adjusted to a value of 1.5 with hydrochloric acid (2 M). Then dipotassium hydrogen phosphate trihydrate (136.5 mg, 0.6 mmol) was dissolved in 2 mL water and added to the calcium containing solution. Sodium hydroxide (2 M) was added dropwise under vigorous stirring until the pH reached a value of 12. The particles were washed 4 times with ethanol by centrifugation at 19,000 rpm (43,146 RCF) for 10 minutes and finally redispersed in 20 mL ethanol.

1.4 Loading of Calcium Phosphate-Citrate Particles with Ibuprofen:

Calcium phosphate-citrate particles were loaded with ibuprofen in hexane, and release of the drug was shown with UV-Vis methods. The maximal loading was 15.6 w % (FIG. 5).

For this purpose, 2.5 mg of calcium phosphate-citrate particles were redispersed in 1 mL hexane and loaded with ibuprofen (4 mg, 19.4 µmol) for 24 hours. The particles were separated by centrifugation at 14,000 rpm (16,873 RCF) for 3 minutes and washed with 1 mL hexane. After a second step of centrifugation the supernatant was discarded and the particles were dried at 60° C. The dried particles were transferred into the cap of a home built UV-Vis setup (2.5 mg particles in 200 µL simulated body fluid, SBF) and separated by a cellulose membrane from the measuring cell. Ibuprofen released from the particles diffuses through the membrane and can be detected in the measuring cell (FIG. 6). While detecting the absorption of ibuprofen at 264 nm over time, the release was quantified.

1.5 Preparation of Calcium Phosphate-Citrate Particles (with Lipid Membrane) for Release and Cell Experiments:

Furthermore, we formed a stable lipid membrane around the particles with a modified "solvent exchange" method, which retains the drug inside the particles until an external stimulus disrupts the lipid membrane.

The amount of 0.5 mg of calcium phosphate-citrate particles was loaded in 1 mL aqueous calcein solution (0.62 mg, 1 mmol, pH 9.4) and cetyltrimethylammonium chloride (6.25 µg, 19.5 nmol) for 30 minutes. The particles were separated by centrifugation at 14,000 rpm (16,873 RCF) for 3 minutes. The loaded particles were redispersed in 200 µL of a 3:1 vol % lipid solution of 1,2-dioleoyl-3-trimethylammonium-propane (DOTAP, 12.5 mg/mL 60/40 $H_2O$/EtOH Vol % solution) and 1,2-dioleoyl-sn-glycero-3-phosphocholine (DOPC, 12.5 mg/mL 60/40 $H_2O$/EtOH Vol %), and SBF (900 µL, pH 7.4) was added. The calcium phosphate-citrate-lipid particles were washed twice by centrifugation at 12,000 rpm (12,396 RCF) for 5 minutes with SBF (500 µL, pH 7.4).

1.6 In Vitro Release Fluorescence Measurements:

With in vitro release experiments we verified the effective encapsulation and release of model drugs (FIG. 7):

Calcium phosphate-citrate-lipid particles were transferred into the cap of a homebuilt fluorescence setup (0.5 mg particles in 200 µL SBF) and separated from the measuring cell by a cellulose membrane (molecular weight cut off 14,000) (FIG. 6). Dye that is released from the particles diffuses through the membrane and can be detected in the measuring cell. While detecting the evolution of calcein fluorescence at 512 nm (excitation at 495 nm) against time the stimulated release can be observed (FIG. 6).

1.7 Cell Uptake and Viability Tests:

Particle uptake and cell viability were investigated with several cell lines after an incubation time of 48 hours (particle uptake, FIG. 8) and 72 hours (cell viability, FIG. 9).

For cell experiments, cells were grown in the respective medium as recommended by American Type Culture Collection (ATCC) and Japanese Collection of Research Bioresources (JCRB). They were seeded onto microscopy slides or 96-well plates, and one day after seeding the particles were added. Spinning-Disc-Microscopy showed efficient uptake of lipid-coated calcium phosphate-citrate-lipid particles (FIG. 8), whereas uncoated calcium phosphate-citrate particles were not taken up. MTT assays confirmed cell death 72 hours after treatment with lipid-coated particles, whereas uncoated particles did not affect cell viability (FIG. 9 and Table 2).

1.8 Stability and Crystallization

Figure 10:
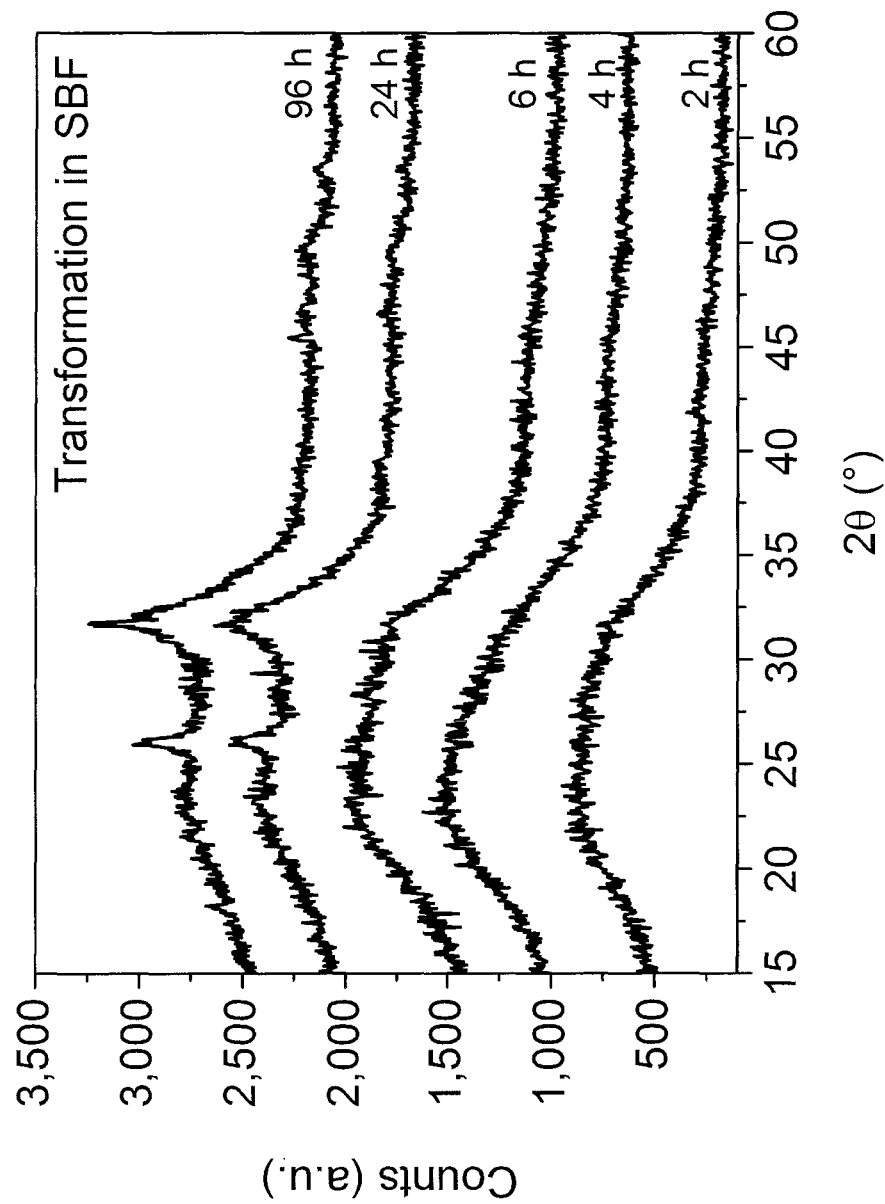

We performed stability tests with our calcium phosphate-citrate nanoparticles in SBF over four days and investigated the crystallization process (FIG. 10).

20 mg of calcium phosphate-citrate particles were transferred to 20 mL SBF. After 2, 4, 6, 24, and 96 hours each time 1 mL of the suspension was withdrawn and the particles were washed twice by centrifugation at 14,000 rpm (16,873 RCF) for 5 minutes with 1 mL ethanol. The particles were dried at 60° C. Within the monitored time period we observed the phase transformation from amorphous calcium phosphate-citrate into crystalline apatite, which is of central importance for bone growth.

Example 2

2.1 Characterization Techniques:

Nitrogen sorption measurements were performed on a Quantachrome Instrument NOVA 4000e at 77 K. Samples (25 mg) were outgassed at 120° C. for 12 h in vacuo (10 mTorr).

Pore size and pore volume were calculated by a QSDFT equilibrium model of $N_2$ on carbon, based on the desorption branch of the isotherms. The QSDFT method takes into account the effects of surface roughness and heterogeneity (Quantachrome, 2012). Cumulative pore volumes were evaluated up to a pore size of 10 nm, in order to remove the contribution of interparticle textural porosity.

Surface areas were calculated with the BET model in the range $p/p_0$=0.05-0.2 (Brunauer et al., 1938).

Thermogravimetric analysis of the samples was performed on a Netzsch STA 440 C TG/DSC in a stream of synthetic air with a heating rate of 10 K/min.

Dynamic light scattering measurements were performed on a Malvern Zetasizer-Nano instrument with a 4 mW Ne—He laser (633 nm) in ethanolic suspension at a concentration of 0.5 mg mL$^{-1}$.

Scanning electron microscope images were obtained on a JEOL JSM-6400F. For sample preparation a droplet of the ethanolic colloidal suspension was placed on a 60° C. preheated carbon pad. Samples were sputtered with carbon before measurement.

Transmission electron microscopy was performed on a JEOL JEM 2011 at an acceleration voltage of 200 kV. For sample preparation a droplet of a diluted ethanolic colloidal suspension was deposited on a carbon-coated copper grid, and the solvent was allowed to evaporate.

EDX spectra were recorded with an EDAX Apollo XLT SDD Detector (30 mm$^2$)

For ICP measurements the samples were dissolved in concentrated HNO$_3$ and heated at 110° C. for 30 minutes. After dilution with H$_2$O, the data collection was carried out with a Varian Vista RL ICP-OES with radially viewed plasma.

Infrared spectra were measured with a Thermo Scientific Nicolet iN 10 infrared microscope.

XRD patterns were obtained with a Bruker D8 Discover X-ray diffractometer using Cu-K$_\alpha$ radiation (1.5406 Å).

$^{13}$C, $^{31}$P, and $^1$H solid-state NMR (ssNMR) measurements were performed on a Bruker DSX Avance500 FT spectrometer in a 4 mm ZrO$_2$ rotor under magic angle spinning conditions. $^{13}$C ssNMR data were obtained at 125.8 MHz under cross-polarization conditions with 52000 transients. $^{31}$P ssNMR data were acquired at 202.5 MHz under cross-polarization conditions with 8 transients. $^1$H ssNMR data were obtained at 500.2 MHz with 1 run.

2.2 IR-Spectra:

The obtained IR-spectra (FIG. 2) are normalized to the PO$_4^{3-}$ stretching vibration at 1083 cm$^{-1}$ (Socrates 2001; Jansen and Leâon, 2009). The peak at 556 cm$^{-1}$ is attributed to the bending vibration of the PO$_4^{3-}$ group (Hu et al., 2010; Davies et al., 2014). The vibrations at 1414 cm$^{-1}$ and 1590 cm$^{-1}$ are attributed to the symmetrical- and the anti-symmetrical stretching of COO$^-$ groups from the incorporated citric acid in the structure (Socrates 2001; Nakamoto 2009). The vibrations at 3100 cm$^{-1}$ to 2800 cm$^{-1}$ result from the C—H vibrations of citric acid. We synthesized crystalline apatite of which the C—O vibrations compared to calcium phosphate-citrate drastically decreased. The visible C—O bands result from carbonate containing crystalline apatite (Weng et al., 2002). The PO$_4^{3-}$ vibration is shifted to lower wavenumbers at 1033 cm$^{-1}$ indicating crystalline apatite (Gadaleta et al., 1996).

2.3 Elemental Analysis:

The ratio of Ca:P in calcium phosphate-citrate particles is 1.61, it was determined with EDX and ICP methods (Table 1). Therefore, the particles are similar to the stoichiometric value for apatite, of Ca:P of 1.66.

TABLE 1

Atomic ratio of calcium and phosphor with EDX and ICP methods.

| measurement | | calcium (atom %) | phosphor (atom %) | Ca:P |
|---|---|---|---|---|
| EDX | I | 8.69 | 5.30 | 1.64 |
| | II | 7.04 | 4.39 | 1.60 |
| | III | 8.69 | 5.43 | 1.60 |
| | IV | 6.04 | 3.81 | 1.58 |
| | V | 3.59 | 2.21 | 1.62 |
| | VI | 6.20 | 3.91 | 1.58 |
| | VII | 8.69 | 5.43 | 1.60 |
| ICP | I | 6.21 | 3.89 | 1.59 |
| | II | 6.19 | 3.85 | 1.60 |
| average (EDX) | | 6.99 | 4.35 | 1.61 |
| average (ICP) | | 6.20 | 3.87 | 1.60 |

2.4 Thermogravimetric Analysis:

The incorporation of citric acid into the framework of the hybrid calcium phosphate-citrate particles was additionally visualized with TGA measurements (FIG. 11). The mass loss of calcium phosphate-citrate particles before and after the extraction was investigated with TGA. A moderate mass loss up to 200° C. is attributed to adsorbed water and weakly bound organics (7 w %). Between 200° C. and 750° C. significant mass loss is observed which we attribute to strongly bound organics. Above 750° C. the mass loss stays constant up to 900° C. Before the extraction of CTAC and Pluronic F127 the mass loss of the organics adds up to 36 w %. For particles that have been extracted the mass loss of organics is lowered to 20 w % which we attribute to the decomposition of citric acid. Due to the incorporation of citric acid in the calcium phosphate-citrate structure, the mass loss is shifted to higher temperatures compared to pure citric acid (decomposition temperature: 175° C.). Therefore, we can estimate the amount of CTAC/Pluronic F127 in the pore structure to be 16 w %.

Figure 12:
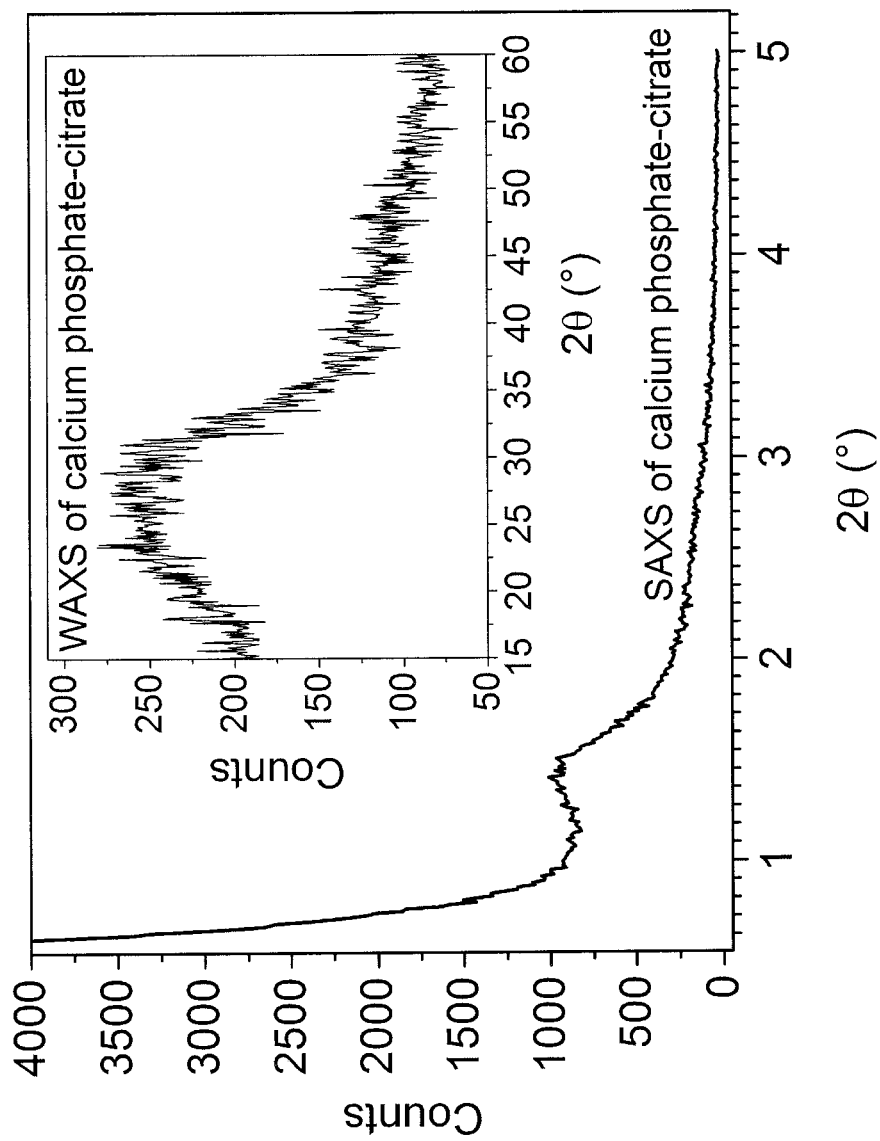

2.5 X-Ray Scattering:

In small angle X-Ray scattering data, a broad reflection is observed at 2θ=1.44, which is calculated to correspond to a d-spacing of 6.13 nm. With a pore size of 5 nm obtained from N$_2$-sorption measurements, a wall thickness of 1.13 nm is calculated. In wide angle X-ray scattering the typical peak shape for amorphous compounds is observed (FIG. 12).

2.6 ssNMR:

The resonance of PO$_4^{3-}$ is located at 1.62 ppm in the $^{31}$P ssNMR spectrum (FIG. 3a). Using $^{13}$C ssNMR, we demonstrate the successful implementation of citric acid. The resonance of the primary C-atoms is located at 179 ppm, the secondary C-atoms are located at 44 ppm, and the tertiary C-atom is located at 74 ppm (FIG. 3b). The $^1$H ssNMR shows the resonance of structural O—H at 1.14 ppm and a small shoulder from adsorbed H$_2$O (FIG. 3c).

2.7 Cell Viability:

Cell viability assays (MTT) were carried out all together for eight cell lines. See FIG. 9.

Figure 13:
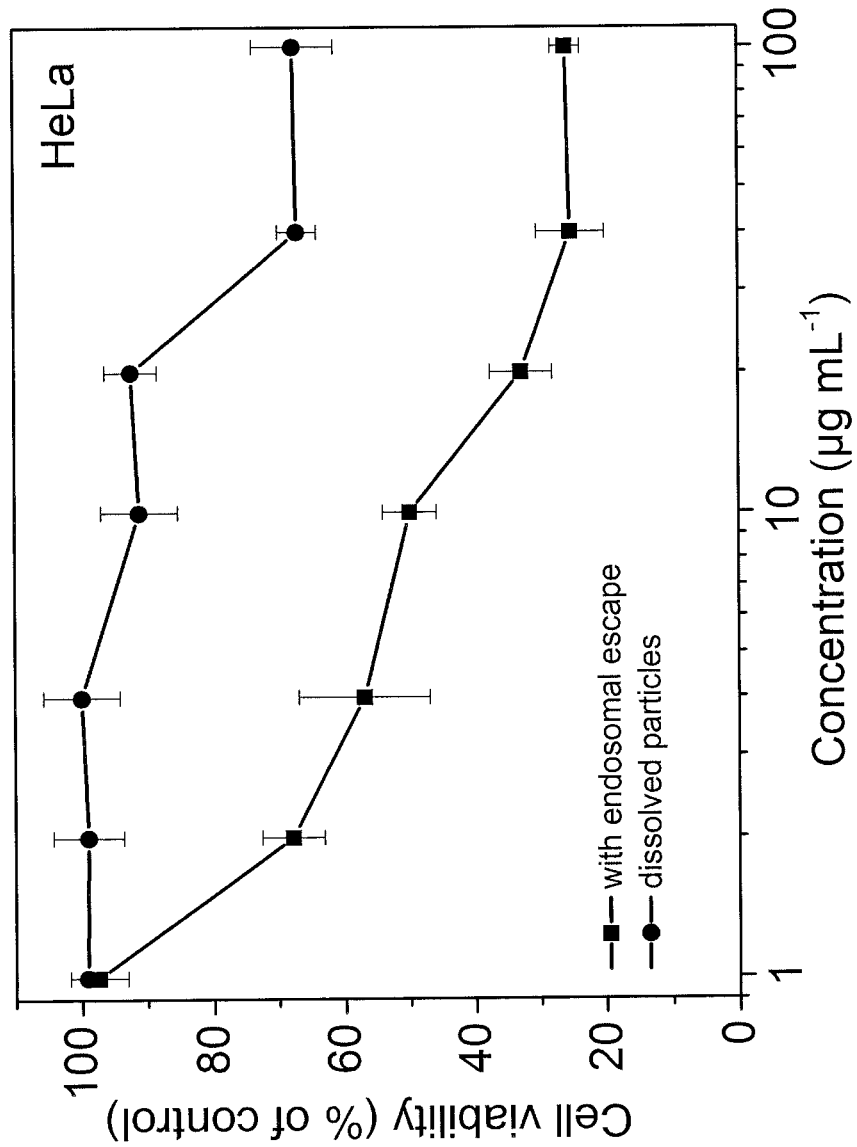

In a reference experiment we dissolved 1 mg of calcium phosphate-citrate-lipid particles loaded with calcein and CTAC in 0.1 M HCl. These particles had the same composition as the ones that induce apoptosis in cancerous cells within 72 hours. HeLa cells were treated with this solution that exhibited the same concentration as the particle solution that contained undissolved particles. The previously dissolved particles had no effect on cell viability in HeLa cells up to concentrations of ~100 μg mL$^{-1}$, while the calcium phosphate-citrate-lipid particles induced apoptosis with an IC$_{50}$ of 8.0 μg mL$^{-1}$ (FIG. 13). In conclusion, the additive CTAC, the dissolved model drug calcein, and the calcium ions did not affect cell viability, if cells were treated directly. In contrast, with optimized calcium phosphate-citrate-lipid nanoparticles that are able to escape from the endosome we show effective cell death with low $IC_{50}$ values (Table 2).

Example 3

We have also synthesized amorphous mesoporous calcium phosphate-citrate nanoparticles without the presence of a surfactant template. This is demonstrated with nitrogen sorption data for mesoporosity without a template, see FIG. 15 a.

3.1 Synthesis of Mesoporous Calcium Phosphate-Citrate Nanoparticles without a Surfactant Template:

The synthesis of the colloidal and spherical calcium phosphate-citrate compound was achieved with an adjusted Pechini process (Pechini 1967; Yang et al., 2011) See also U.S. Pat. No. 3,330,697 A.

In a 50 mL polypropylene reactor citric acid (CA, 240 mg, 1.25 mmol), $Ca(NO_3)_2 \cdot 4 H_2O$ (295 mg, 1.25 mmol) and $(NH_4)H_2PO_4$ (86.3 mg, 0.75 mmol) were dissolved in water (20 mL, 1.11 mmol) to obtain solutions with a Ca:CA molar ratio of 1:1. Then ethylene glycol (7.15 g, 115 mmol) was added under stirring. This solution was added under stirring to triethanolamine (7.15 g, 48 mmol). The suspension was stirred at 500 rpm at room temperature for 10 minutes. Then the suspension was diluted approximately 1:1 with ethanol. The particles were separated by centrifugation at 19,000 rpm (43,146 RCF) for 15 minutes and redispersed in $NH_4NO_3$/EtOH (2 w %, 80 mL). The suspension was heated under reflux conditions at 90° C. for 30 minutes. Then the particles were separated by centrifugation at 19,000 rpm (43,146 RCF) for 10 minutes and redispersed in 80 mL ethanol. The mixture was heated under reflux conditions at 90° C. for 30 minutes. The particles were separated by centrifugation at 19,000 rpm (43,146 RCF) for 10 minutes and redispersed in 20 mL ethanol.

3.2 Cell Experiments:

These particles were also taken up by HeLa cells, and they killed the cells as efficiently as the particles prepared with a template, see FIG. 15 b. The loading and preparation of these particles for cell uptake was identical to Example 1 Section 1.5.

Example 4

The $Ca^{2+}$ ion can be substituted or replaced with $Mg^{2+}$ or the $Ca^{2+}$ ion can be mixed with $Mg^{2+}$. The resulting nanoparticles can thus be colloidal amorphous mesoporous magnesium phosphate-citrate nanoparticles.

4.1 Synthesis of Mesoporous Magnesium Phosphate-Citrate Nanoparticles:

The synthesis of the colloidal and spherical magnesium phosphate-citrate compound was achieved with an adjusted Pechini process (Pechini 1967; Yang et al., 2011) See also U.S. Pat. No. 3,330,697 A.

Figure 16:
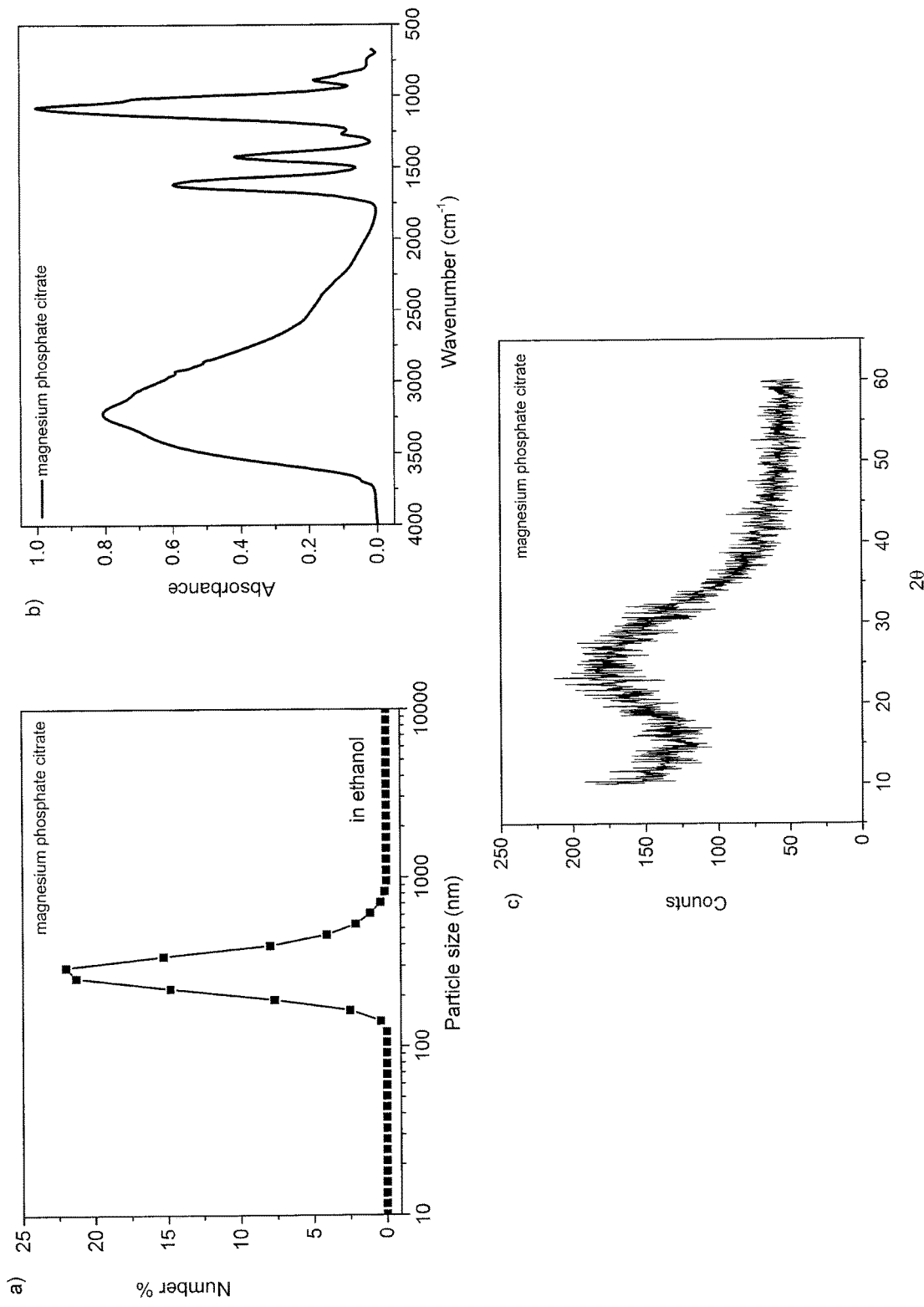
Figure 18:
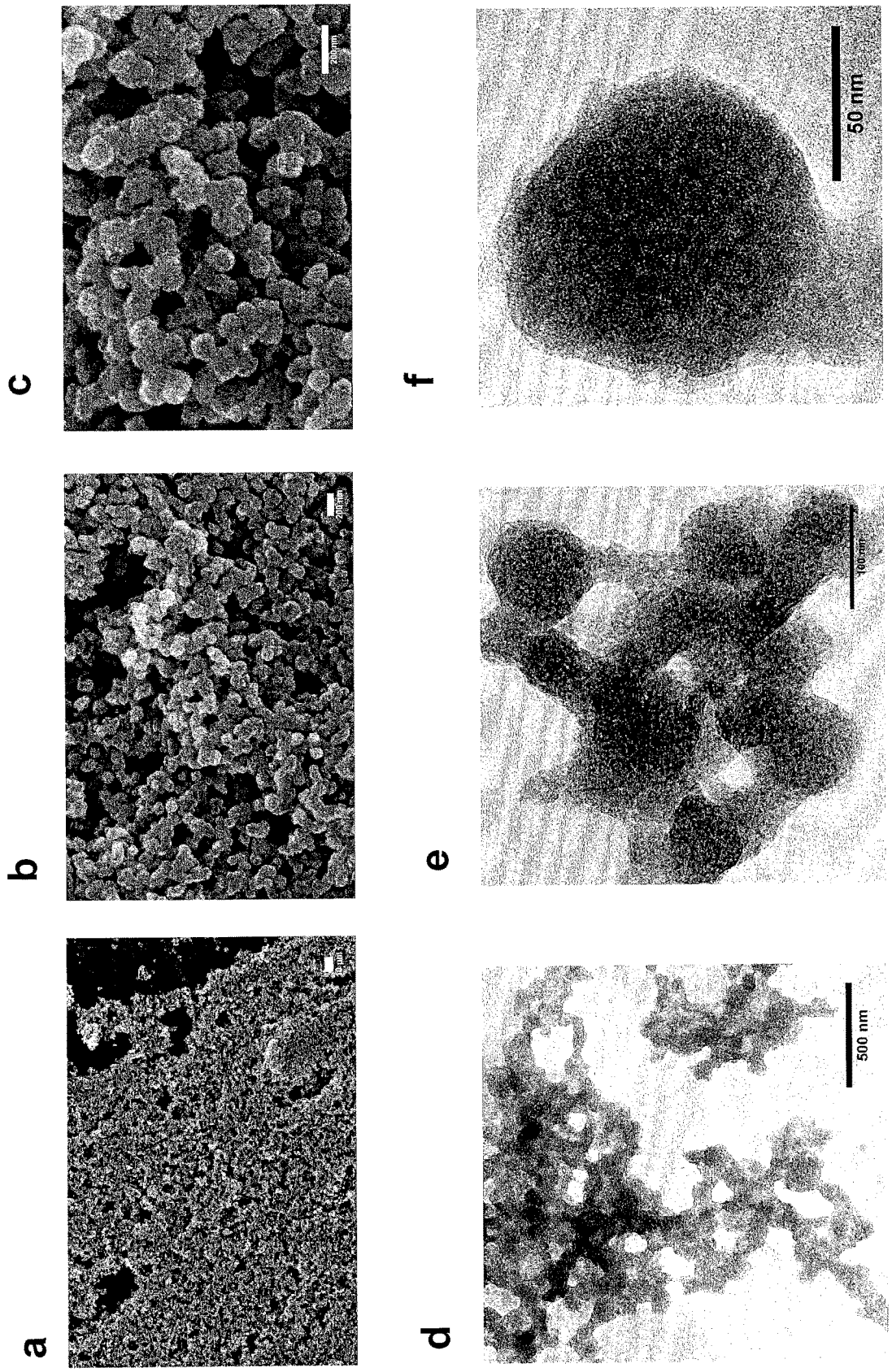

In a 50 mL polypropylene reactor citric acid (CA, 270 mg, 1.40 mmol), $Mg(NO_3)_2 \cdot 6 H_2O$ (320 mg, 1.25 mmol) and $(NH_4)H_2PO_4$ (142 mg, 1.23 mmol) were dissolved in water (20 mL, 1.11 mmol). Then cetyltrimethylammonium chloride (622 mg, 1.94 mmol) and ethylene glycol (7.15 g, 115 mmol) were added under stirring. This solution was added under stirring to triethanolamine (7.15 g, 48 mmol) and ethanolamine (3 g, 49 mmol). The suspension was stirred at 500 rpm at room temperature for 10 minutes. Then the suspension was diluted approximately 1:1 with ethanol. The particles were separated by centrifugation at 19,000 rpm (43,146 RCF) for 15 minutes and redispersed in $NH_4NO_3$/EtOH (2 w %, 80 mL). To extract the template, the suspension was heated under reflux conditions at 90° C. for 30 minutes. Then the particles were separated by centrifugation at 19,000 rpm (43,146 RCF) for 10 minutes and redispersed in 80 mL ethanol. The mixture was heated under reflux conditions at 90° C. for 30 minutes. The particles were separated by centrifugation at 19,000 rpm (43,146 RCF) for 10 minutes and redispersed in 20 mL ethanol. (FIGS. 16-18).

4.2 Cell Experiments:

These particles were also taken up by HeLa cells, and they killed the cells efficiently, see FIG. 19. The loading and preparation of these particles for cell uptake was identical to Example 1 Section 1.5.

Example 5

The $Ca^{2+}$ ion can be substituted or replaced with $Mg^{2+}$ or the $Ca^{2+}$ ion can be mixed with $Mg^{2+}$. The resulting nanoparticles can thus be colloidal amorphous mesoporous calcium-magnesium phosphate-citrate nanoparticles.

5.1 Synthesis of Mesoporous Calcium-Magnesium Phosphate-Citrate Nanoparticles:

The synthesis of the colloidal and spherical calcium-magnesium phosphate-citrate compound was achieved with an adjusted Pechini process (Pechini 1967; Yang et al., 2011) See also U.S. Pat. No. 3,330,697 A.

In a 50 mL polypropylene reactor citric acid (CA, 270 mg, 1.40 mmol), $Ca(NO_3)_2 \cdot 4 H_2O$ (236 mg, 1.00 mmol), $Mg(NO_3)_2 \cdot 6 H_2O$ (64 mg, 0.25 mmol) and $(NH_4)H_2PO_4$ (142 mg, 1.23 mmol) were dissolved in water (20 mL, 1.11 mmol). Then cetyltrimethylammonium chloride (622 mg, 1.94 mmol) and ethylene glycol (7.15 g, 115 mmol) were added under stirring. This solution was added under stirring to triethanolamine (7.15 g, 48 mmol). The suspension was stirred at 500 rpm at room temperature for 10 minutes. Then the suspension was diluted approximately 1:1 with ethanol. The particles were separated by centrifugation at 19,000 rpm (43,146 RCF) for 15 minutes and redispersed in $NH_4NO_3$/EtOH (2 w %, 80 mL). To extract the template, the suspension was heated under reflux conditions at 90° C. for 30 minutes. Then the particles were separated by centrifugation at 19,000 rpm (43,146 RCF) for 10 minutes and redispersed in 80 mL ethanol. The mixture was heated under reflux conditions at 90° C. for 30 minutes. The particles were separated by centrifugation at 19,000 rpm (43,146 RCF) for 10 minutes and redispersed in 20 mL ethanol. (FIG. 20-22a).

5.2 Cell Experiments:

These particles were also taken up by HeLa cells, and they killed the cells efficiently, see FIG. 22b. The loading and preparation of these particles for cell uptake was identical to Example 1 Section 1.5.

5.3 Elemental Analysis:

The ratio of Ca/Mg:P in calcium-magnesium phosphate-citrate particles is 1.51, it was determined with EDX methods (Table 3). In calcium-magnesium phosphate-citrate particles calcium was replaced by 23 atom % with magnesium.

TABLE 3

Atomic ratio of calcium and phosphor with EDX and ICP methods.

| measurement | calcium (atom %) | magnesium (atom %) | phosphor (atom %) | Ca/Mg:P |
|---|---|---|---|---|
| average (EDX) | 3.6 | 1.1 | 3.1 | 1.51 |

The features disclosed in the foregoing description, in the claims and/or in the accompanying drawings may, both separately and in any combination thereof, be material for realizing the invention in diverse forms thereof.

REFERENCES

Arcos, D. & Vallet-Regi, M. Bioceramics for drug delivery. *Acta Mater.* 61, 890-911 (2013). Behr, J.-P. The proton sponge: a trick to enter cells the viruses did not exploit. CHIMIA 51, 34-36 (1997).

Brunauer, S., Emmett, P. & Teller, E. Adsorption of Gases in Multimolecular Layers. *J. Am. Chem. Soc.* 60, 309-319 (1938).

Cauda, V. et al. Colchicine-loaded lipid bilayer-coated 50 nm mesoporous nanoparticles efficiently induce microtubule depolymerization upon cell uptake. *Nano Lett.* 10, 2484-2492 (2010).

R. Chari, M. Miller, W. Widdison, *Angew. Chem. Int. Ed.* 2014, 53, 3796-3827.

Chen, F. et al. Multifunctional biodegradable mesoporous microspheres of $Eu^{3+}$-doped amorphous calcium phosphate: microwave-assisted preparation, pH-sensitive drug release, and bioimaging application. *J. Mater. Chem. B* 2, 7132-7140 (2014).

Chen, L. et al. Nanostructured calcium phosphate carriers for deliver of poor water-soluble drug silybin. *Mater. Lett.* 143, 252-255 (2015).

Coley, H. M. Mechanisms and strategies to overcome chemotherapy resistance in metastatic breast cancer. *Cancer Treat. Rev.* 34, 378-390 (2008).

Davies, E. et al. Citrate bridges between mineral platelets in bone. *PNAS* 14, 1354-1363 (2014).

Delgado-López, J. M. et al. Crystallization of bioinspired citrate functionalized nanoapatite with tailored carbonate content. *Acta Biomater.* 8, 3491-3499 (2012).

Ding, G. et al. Porous microspheres of amorphous calcium phosphate: Block copolymer templated microwave-assisted hydrotheinial synthesis and application in drug delivery. *J. Colloid. Interface Sci.* 443, 72-79 (2015).

Dorozhkin, S. V. & Epple, M. Biological and medical significance of calcium phosphates. *Angew. Chem. Int. Ed.* 41, 3130-3146 (2002).

Gadaleta, S., Paschalis, E., Betts, F., Mendelsohn, R. & Boskey, A. Fourier transfoim infrared spectroscopy of the solution-mediated conversion of amorphous calcium phosphate to hydroxyapatite: new correlations between X-ray diffraction and infrared data. *Calcif. Tissue Int.* 58, 9-16 (1996).

Gruenberg, J. The endocytic pathway: a mosaic of domains. *Nat. Rev. Mol. Cell Biol.* 2, 721-730 (2001).

Gupta, B. P. et al. Identification of selective inhibitors of cancer stem cells by high-throughput screening. *Cell* 138, 645-659 (2009).

He, Q. et al. The effect of PEGylation of mesoporous silica nanoparticles on nonspecific binding of serum proteins and cellular responses. *Biomaterials* 31, 1085-1092 (2010).

Hu, Y. Y., Rawal, A., Schmidt-Rohr, K. Strongly bound citrate stabilizes the apatite nanocrystals in bone. *Proc. Natl. Acad. Sci.* 107, 22425-22429 (2010).

Iafisco, M. et al. Smart delivery of antitumoral platinum complexes from biomimetic hydroxyapatite nanocrystals. *J. Mater. Chem.* 19, 8385-8392 (2009).

IUPAC Recommendations. *Pure Appl. Chem.*, Vol. 79, No. 10, pp. 1801-1829, 2007):

Jacobs E E, Woodman J L & Kuhn L T. Sodium citrate stabilized calcium phosphate nanoparticles for the sustained delivery of cisplatin. Society for *Biomaterials*, Abstract #57 (2013).

Jansen, J. & Leâon, B. *Thin calcium phosphate coatings for medical implants* (Springer, 2009).

Kokubo, T. & Takadama, H. How useful is SBF in predicting in vivo bone bioactivity?. *Biomaterials* 27, 2907-2915 (2006).

Kopp, F. et al. Sequential Salinomycin Treatment Results in Resistance Formation through Clonal Selection of Epithelial-Like Tumor Cells. *Transl. Oncol.* 7, 702-711 (2014).

Koutsopoulos S & Dalas E. The crystallization of hydroxyapatite in the presence of lysine. *J. Coll Interface Science* 231, 207-212 (2000).

Li, J., Yang, Y. & Huang, L. Calcium phosphate nanoparticles with an asymmetric lipid bilayer coating for siRNA delivery to the tumor. *J. Control. Release* 158, 108-114 (2012).

Lin, Y. S. & Haynes, C. L. Impacts of mesoporous silica nanoparticle size, pore ordering, and pore integrity on hemolytic activity. *J. Am. Chem. Soc.* 132, 4834-4842 (2010).

Lopez-Macipe, A., Gomez-Morales, J. & Rodriguez-Clemente, R. The role of pH in the adsorption of citrate ions on hydroxyapatite. *J. Colloid Interf. Sci.* 200,114-120 (1998).

Mackowiak, S. A. et al. Targeted drug delivery in cancer cells with red-light photoactivated mesoporous silica nanoparticles. *Nano Lett.* 13, 2576-2583 (2013).

Matsuo, H. et al. Role of LBPA and Alix in multivesicular liposome formation and endosome organization. *Science* 303, 531-534 (2004).

McIlvaine, T. C. A buffer solution for colorimetric comparison. *J. Biol. Chem.* 49, 183-186 (1921).

Meyer J L & Eanes E D. A thermodynamic analysis of the amorphous to crystalline calcium phosphate transformation. *Calcif. Tiss. Res.* 25, 59-68 (1978).

Moeller, K., Kobler, J. & Bein, T. Colloidal suspensions of nanometer-sized mesoporous silica. *Adv. Funct. Mater.* 17, 605-612 (2007).

Mitsionis A I, Vaimakis T C & Trapalis C C. The effect of citric acid on the sintering of calcium phosphate ceramics. *Ceramics International* 36, 623-634 (2010).

Motskin, M. et al. Hydroxyapatite nano and microparticles: correlation of particle properties with cytotoxicity and biostability. *Biomaterials* 30, 3307-3317 (2009).

Nakamoto, K. *Infrared and Raman Spectra of Inorganic and Coordination Compounds* (6 ed., John Wiley & Sons, Inc, 2009).

Orrenius, S., Zhivotovsky, B. & Nicotera, P. Regulation of cell death: the calcium-apoptosis link. *Nat. Rev. Mol. Cell. Biol.* 4, 552-565 (2003)

Palmer, L. C. et al. Biomimetic systems for hydroxyapatite mineralization inspired by bone and enamel. *Chem. Rev.* 108, 4754-4783 (2008).

Pechini, M. P. Method of preparing lead and alkaline earth titanates and niobates and coating method using the same to form a capacitor. U.S. Pat. No. 3,330,697, (1967).

Quantachrome, Application of QSDFT (quenched solid density functional theory)—a novel density functional theory for an accurate pore size analysis of disordered porous carbons. (Quantachrome Instruments USA, 2012)

Rodríguez-Ruiz, I. et al. pH-responsive delivery of doxorubicin from citrate-apatite nanocrystals with tailored carbonate content. *Langmuir* 29, 8213-8221 (2013).

Rouquérol, J. et al. Recommendations for the characterisation of porous solids. *Pure Appl. Chem.* 66, 1739-1758 (1994).

Schlossbauer, A. et al. A programmable DNA-based molecular valve for colloidal mesoporous silica. *Angew. Chem. Int. Ed.* 49, 4734-4737 (2010).

Schlossbauer, A. et al. Cascaded photoinduced drug delivery to cells from multifunctional core-shell mesoporous silica. *Adv. Healthcare Mater.* 1, 316 (2012).

Sing, K. S. W. et al. Reporting physisorption data for gas/solid systems with special reference to the determination of surface area and porosity. *Pure Appl. Chem.* 57, 603-619 (1985).

Slowing, I. I., Trewyn, B. G. & Lin, V. S. Y. Effect of Surface Functionalization of MCM-41-Type Mesoporous Silica Nanoparticles on the Endocytosis by Human Cancer Cells. *J. Am. Chem. Soc.* 128, 14792-14793 (2006).

Slowing, I. I., Vivero-Escoto, J. L., Wu, C.-W. & Lin, V. S. Y. Mesoporous silica nanoparticles as controlled release drug delivery and gene transfection carriers. *Adv. Drug Deliver. Rev.* 60, 1278-1288 (2008).

Socrates, G. *Infrared and Raman characteristic group frequencies: tables and charts* (3 ed., Wiley, 2001).

Sonawane, N. D., Szoka, F. C. & Verkman, A. S. Chloride accumulation and swelling in endosomes enhances DNA transfer by polyamine-DNA polyplexes. *J. Biol. Chem.* 278, 44826-44831 (2003).

Sun, H. et al. Oligonucleotide Aptamers: New Tools for Targeted Cancer Therapy. *Molecular Therapy Nucleic Acids* 3, e182 (2014).

Sorkin, A. & von Zastrow, M. Signal transduction and endocytosis: close encounters of many kinds. *Nat. Rev. Mol. Cell Biol.* 3, 600-614 (2002).

Tang, W. et al. Differential cytotoxicity and particle action of hydroxyapatite nanoparticles in human cancer cells. *Nanomedicine* 9, 397-412 (2014).

Torchilin, V. P. Multifunctional, stimuli-sensitive nanoparticulate systems for drug delivery. *Nat. Rev. Drug Discov.* 13, 813-827 (2014).

Varkouhi, A. K., Scholte, M., Stoma, G. & Haisma, H. J. Endosomal escape pathways for delivery of biologicals. *J. Control. Release* 151, 220-228 (2011).

Wang P, Li C, Gong H, Jiang X, Wang H & Li K. Effects of synthesis conditions on the morphology of hydroxyapatite nanoparticles by wet chemical process. *Powder Technology* 203, 315-321 (2010).

Weng, W., Han, G., Du, P. & Shen, G. The effect of citric acid addition on the formation of sol-gel derived hydroxyapatite. *Mater. Chem. Phys.* 74, 92-97 (2002).

Xie, B. & Nancollas, G. How to control the size and morphology of apatite nanocrystals in bone. *Proc. Natl. Acad. Sci.* 107, 22369-22370 (2010).

Yang, P., Yang, P., Teng, X., Lin, J. & Huang, L. A novel luminescent mesoporous silica/apatite composite for controlled drug release. *J. Mater. Chem.* 21, 5505-5510 (2011).

Yuan H, van den Doel M, Li S, van Blitterswijk C A, de Groot K, de Bruijn J D. A comparison of the osteoinductive potential of two calcium phosphate ceramics implanted intramuscularly in goats. *J Material Science: Materials in Medicine* 13, 1271-1275 (2002).

Zhang, Y., Schwerbrock, N. M., Rogers, A. B., Kim, W. Y. & Huang, L. Codelivery of VEGF siRNA and gemcitabine monophosphate in a single nanoparticle formulation for effective treatment of NSCLC. *Mol. Ther.* 21, 1559-1569 (2013).

Zhao, X., Zhu, Y., Chen, F. & Wu J. Calcium phosphate nanocarriers dual-loaded with bovine serum albumin and ibuprofen: facile synthesis, sequential drug loading and sustained drug release. *Chem. Asian J.* 7, 1610-1615 (2012).

Zhao, X. et al. Cytotoxicity of hydroxyapatite nanoparticles is shape and cell dependent. *Arch. Toxicol.* 87, 1037-1052 (2013-a).

Zhao, X., Zhu Y., Chen F., Lu B. & Wu J. Nanosheet-assembled hierarchical nanostructures of hydroxyapatite: surfactant-free microwave-hydrothermal rapid synthesis, protein/DNA adsorption and pH-controlled release. *Cryst. Eng. Comm.* 15, 206-212 (2013-b).

The invention claimed is:

1. A mesoporous hybrid calcium phosphate-citrate nanoparticle comprising
  (a) calcium phosphate, and
  (b) citrate wherein the calcium phosphate and citrate are interpenetrated on a scale of less than 1 µm such that the mesopores are internal within the nanoparticle, and wherein citrate is incorporated into the structure of the nanoparticle.

2. The nanoparticle of claim 1 having
  a maximum surface area from about 100 to about 1500 m$^2$/g,
  a pore size from about 1 to about 50 nm,
  and/or
  a cumulative pore volume from about 0.1 to 2.0 cm$^3$/g.

3. The nanoparticle of claim 1,
  having a maximum size or diameter from about 5 to about 1000 nm,
  is spherical,
  is amorphous,
  comprising from about 0.01 to about 60 w % of citric acid,
  and/or having IR C—O vibrational bands at around 1590 cm$^{-1}$ and 1400 cm$^{-1}$.

4. The nanoparticle of claim 1 further comprising
  (c1) a lipid bilayer or lipid membrane,
  and/or
  (c2) coating with polymers, capping with proteins, or exosomes/liposomes.

5. The nanoparticle of claim 1 further comprising
  cetyltrimethylammonium halide(s),
  octadecyltrimethylammonium halide(s),
  dodecyltrimethylammonium halide(s),
  reactive oxygen generating molecules or species,
  and/or surfactants or membrane destabilizing agents.

6. The nanoparticle of claim 1 further comprising one or more compounds,
selected from
drugs and prodrugs,
labels,
targeting ligands,
pore-gating molecules,
biocompatible polymers,
anchoring groups at the nanoparticle,
anchoring groups at a lipid bilayer or membrane,
endosomal escape-triggers,
at the nanoparticle and/or at a lipid bilayer or membrane, and
fusion triggering peptides.

7. The nanoparticle of claim 6, wherein, the further compound(s)
is/are in the pores of the nanoparticle
and/or are attached or adsorbed to the nanoparticle or the membrane.

8. A method for synthesizing/generating mesoporous calcium phosphate-citrate nanoparticles according to claim 1, comprising the steps of
(1) mixing calcium ions ($Ca^{2+}$) and phosphate ions ($PO_4^{3-}$) with citrate,
(2) optionally, adding one or more templates,
(3) precipitating the nanoparticles by changing the pH with a base,
(4) optionally, extracting the template(s), and
(5) obtaining the nanoparticles.

9. The method of claim 8, wherein calcium phosphate•citrate is used in step (1),
and/or wherein in step (1)
the molar ratio of $Ca^{2+}$:citric acid is between 1:1 to 1:0.2,
the molar ratio of $Ca^{2+}$:$PO_4^{3-}$ is between 1:0.76 to 1:0.45, and/or
the molar ratio of $Ca^{2+}$:$PO_4^{3-}$:citric acid is about 5:3:5.

10. The method of claim 8, wherein
$Ca(NO_3)_2 \cdot 4H_2O$ is used as a calcium source in step (1),
and/or wherein ($NH_4$)$H_2PO_4$, adenosine-triphosphate, adenosine-diphosphate, and/or adenosine-monophosphate is used as a phosphate source in step (1).

11. The method of claim 8, wherein an $OH^-$ ion is substituted or exchanged with halides or pseudo-halides,
and/or wherein the $Ca^{2+}$ ions are substituted with different divalent cations, and/or
wherein the $PO_4^{3-}$ ions are substituted with carbonate, sulfate, borate, phosphonate, sulfonate, and/or sulfonamide.

12. The method of claim 8, wherein the template(s) added in step (2) are selected from cetyltrimethylammonium halides, Pluronic F127, polyethylene glycol, block copolymers, octadecyltrimethylammonium halides, dodecyltrimethylammonium halide(s) and micelle-enlarging molecules or surfactants,
and/or wherein the template for a pore structure (added in step (2)) varies in chain length,
and/or wherein further biogenic surfactants and different polymers and/or micelle- enlarging molecules are used as further templates.

13. The method of claim 8, comprising the further step of
(6) adding lipid(s) and/or lipid-conjugated molecule(s) to form a lipid bilayer or lipid membrane,
wherein the lipid(s) are selected from 1,2-dioleoyl-3-trimethylammonium-propane (DOTAP), 1,2-dioleoyl-sn-glycero-3-phosphocholine (DOPC), phospholipids, and sphingolipids.
and/or
wherein the lipid-conjugated molecule(s) are selected from cholesterol, collagen, fatty acids, protamine, DNA, pegylated lipid(s), and dye conjugated lipid(s).

14. A nanoparticle obtained by a method of claim 8.

15. A pharmaceutical composition, comprising
(i) at least one nanoparticle of claim 1, and
(ii) a pharmaceutically acceptable carrier and/or excipient.

16. A method of use wherein said method comprises using the nanoparticle of claim 1 in
a drug delivery system
a bone cement or bone implant or teeth cement,
a coating of a medical implant,
a bone material,
a carrier or delivery system with or without taste masking, and/or
a chemotherapeutic.

17. The method, according to claim 16, for use in the diagnosis and/or treatment of cancer.

18. The method according to claim 16, wherein the nanoparticle comprises one or more chemotherapeutic agents, and wherein epithelial and/or mesenchymal cancerous cells are targeted and/or affected.

19. The method according to claim 17, wherein the nanoparticles are released in cancerous cells, from an endosome into the cytosol and nucleus.

20. A method comprising the use of a nanoparticle of claim 1
as a fertilizer or
as an absorber for metal ions from wastewater and/or water.

* * * * *